(12) United States Patent
Dale

(10) Patent No.: US 7,680,308 B2
(45) Date of Patent: Mar. 16, 2010

(54) MEDICAL IMAGING-QUALITY ASSESSMENT AND IMPROVEMENT SYSTEM (QAISYS)

(76) Inventor: Richard B. Dale, 1008 Avalon La., Chesterfield, IN (US) 46017

( * ) Notice: Subject to any disclaimer, the term of this patent is extended or adjusted under 35 U.S.C. 154(b) by 905 days.

(21) Appl. No.: 11/125,527

(22) Filed: May 10, 2005

(65) Prior Publication Data

US 2005/0256743 A1 Nov. 17, 2005

Related U.S. Application Data

(60) Provisional application No. 60/570,013, filed on May 11, 2004.

(51) Int. Cl.
*G06K 9/00* (2006.01)
(52) U.S. Cl. ..................... 382/128; 128/922
(58) Field of Classification Search .................. None
See application file for complete search history.

(56) References Cited

U.S. PATENT DOCUMENTS

| | | | |
|---|---|---|---|
| 5,655,084 A | 8/1997 | Pinsky et al. | |
| 5,786,994 A | 7/1998 | Friz et al. | |
| 6,353,802 B1 | 3/2002 | Barbur et al. | |
| 6,574,304 B1 | 6/2003 | Hsieh et al. | |
| 6,574,629 B1 | 6/2003 | Cooke, Jr. et al. | |
| 7,298,876 B1* | 11/2007 | Marshall et al. ............. | 382/128 |
| 2001/0032101 A1 | 10/2001 | Statius Muller | |
| 2001/0051881 A1 | 12/2001 | Filler | |
| 2002/0082864 A1 | 6/2002 | Kelley et al. | |
| 2002/0085026 A1 | 7/2002 | Bocionek et al. | |
| 2002/0131625 A1 | 9/2002 | Vining et al. | |
| 2002/0194019 A1 | 12/2002 | Evertsz | |
| 2003/0212580 A1 | 11/2003 | Shen | |
| 2004/0015372 A1 | 1/2004 | Bergman et al. | |

* cited by examiner

*Primary Examiner*—Charles Kim
(74) *Attorney, Agent, or Firm*—Edward E. Sowers; Brannon & Associates PC

(57) ABSTRACT

The business method known as QAISys (Quality Assessment and Improvement System) is a process that rates comprehensively and continually the quality of medical images as determined by the interpreting radiologist. The output of this system conveys feedback from the radiologist to the performing technologist and his/her supervisor. This feedback enables medical radiologists, technologists, and managers to bridge any communication gaps between themselves in respect to the quality and effectiveness of medical images. It permits management to assess and track image quality for an entire medical imaging department by modality, location, and/or shift, and for each individual technologist. The QAISys method reveals the nature of recurrent quality failures and highlights which exam types need to be improved. QAISys then indicates practical, cost-effective means of assessing and improving the overall medical images for future patients.

8 Claims, 14 Drawing Sheets

TABLE 1

Radiologist has an opportunity to express his/her degree of dissatisfaction with an exam image at the time of reading the image and assign a Dissatisfaction value

| Numeric Entry | Description of degree of dissatisfaction | Dissatisfaction Value per Exam of dissatisfaction |
|---|---|---|
| 1 | Slightly Compromised (not noted on report) | 0.5 |
| 2 | Moderately Compromised (noted on report) | 1.0 |
| 3 | Severely Compromised (should be repeated) | 3.0 |

Fig. 7

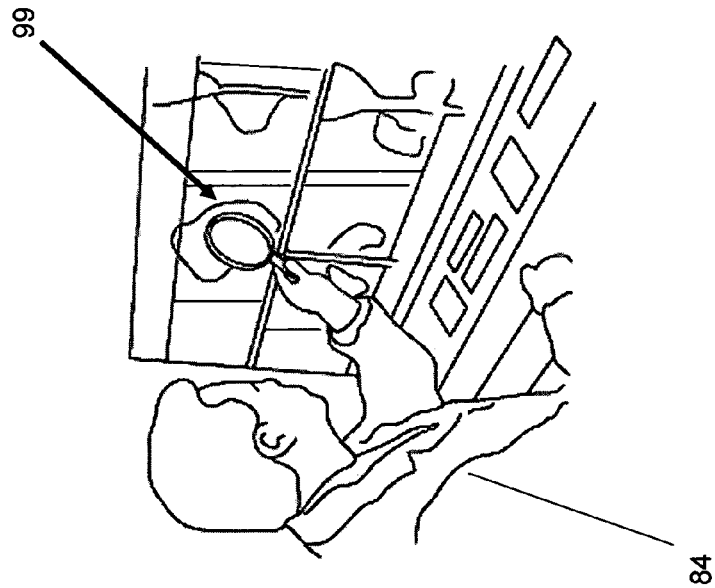

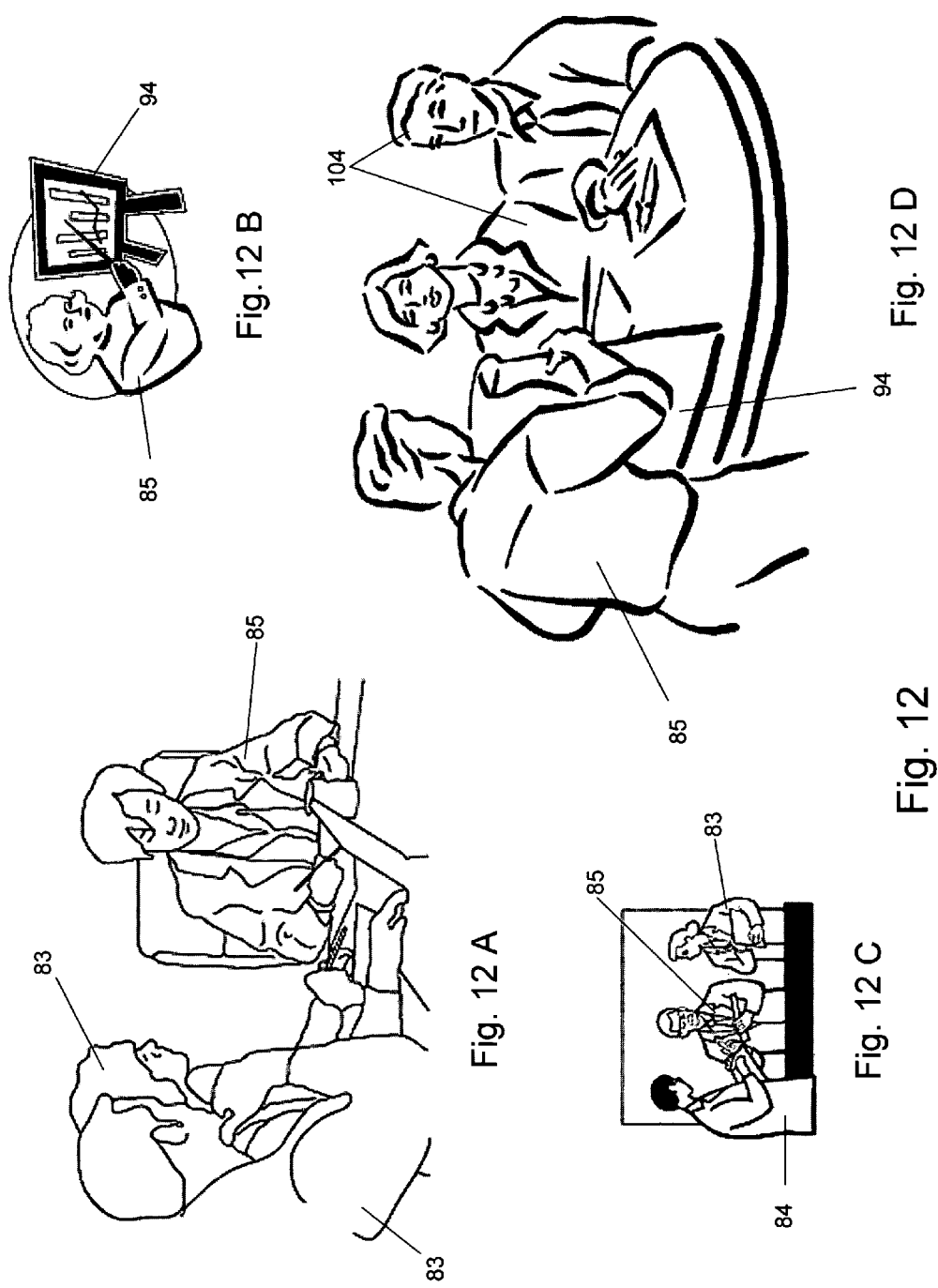

MEDICAL IMAGING-QUALITY ASSESSMENT AND IMPROVEMENT SYSTEM (QAISYS)

CROSS-REFERENCE TO RELATED APPLICATIONS

This application claims the benefit of Provisional Patent Application Ser. No. 60/570,013 filed May 11, 2004 by Richard B. Dale and titled "MEDICAL IMAGING—QUALITY ASSESSMENT and IMPROVEMENT SYSTEM (QAISys)".

FIELD OF INVENTION

This present improvement relates to A BUSINESS METHOD in Health Care Management. Specifically, this new method relates to QUALITY ASSESSMENT and IMPROVEMENT SYSTEM (QAISys) in MEDICAL IMAGING. The method provides a unique way to combine a computer assisted implementation of administering, managing and operating the Quality of Medical Images. The method provides a technique to aid in the feedback, instruction, and improvement to the medical technologists. The method is specific to the individual personal skills of the technologist as these skills relate to the quality of the images that the technologists provide. The method provides a way to combine various existing systems with simple, new analysis to accomplish concrete, useful and tangible results in improvement of the medical images.

FEDERALLY SPONSORED RESEARCH

Not Applicable.

SEQUENCE LISTING OR PROGRAM:

Not Applicable

BACKGROUND

1. Field of Invention

An accurate diagnosis of the condition of a patient is the foundation upon which an appropriate medical treatment stands. Medical imaging is often indispensable in the process of diagnosing and monitoring medical treatment for pathologies and injuries. The diagnostic value of any medical imaging exam is greatly influenced by the competence of the technologist performing it. Over the last few decades, major advances have been made in medical imaging that enable accurate diagnoses to be faster, less invasive, and more cost effective. For radiologists, the workload is not only increasing in the number of exams, but exams are also growing in complexity with the advances in imaging capabilities. It is now being used to assess both anatomy and physiology in patients. The need for exams to be performed correctly the first time cannot be overstated.

Because of these technology improvements, and an aging population, the demand for medical imaging services has increased dramatically creating a shortage of both radiologists and experienced imaging technologists to meet this demand. Radiology workloads are significantly increasing in both volume and complexity. Demands are increasing for more technologists. This demand results in less time and interaction for on the job training and improvement. Further complicating the interaction are the many remote sites for testing at local clinics and specialty test facilities. Satellite sites result in having radiologists often being distant from the technologist during the "reading" of the image. Then, the radiologist may have only an "image" to evaluate and little or no direct input from the technologist that performed the test.

In response to the increasing demand, the latest computer technologies for connectivity are being employed to increase workflow efficiencies. Picture Archiving and Communications Systems (PACS) are being integrated with Radiology Information Systems (RIS) so that images, along with their interpretive reports, patient demographics, and previous exams, can be quickly and easily accessed by radiologists and referring physicians. Often the PACS and RIS are connected to the health care facility's own information system (HIS). While these technologies greatly enhance the communication process, they are not yet being utilized to their full potential.

Modalities is the commonly used term for classification or type of medical and diagnostic imaging tests in the health care industry. Examples and not limitations of key modalities that are completed by medical imaging technologists in preparation for a radiologist to "read" and analyze are as follows:
  a. X-ray digital or conventional film
  b. CR—Computed Radiograpy
  c. CT—Computer Tomography (formerly CAT—Computer Axial Tomography)
  d. MRI—Magnetic Resonance Imaging
  e. US—ultrasound
  f. Mammography—
  g. NM—Nuclear Medicine
  A. Introduction of the Problems Addressed All of the medical imaging modalities require professionals who must be able to use available technology and elicit patient co-operation in order to perform the exam. Technologists must have a good understanding of: the anatomy being imaged, the physics being used to generate the image, and the effects of pathology on the image. They must be able to evaluate the diagnostic quality of the images as the test or exam is being performed. This is a crucial point in the medical imaging process. When image quality is compromised, the technologist must quickly recognize the inadequacy and determine its source. They must then eliminate the cause, or moderate its effect, and repeat the view or imaging sequence as necessary. Proficiency in overcoming these obstacles is vital, especially within the context of tight examination schedules.

A critical need for exams to be performed correctly the first time cannot be overstated. Failure to do so can result in missed diagnoses due to compromised exams. If the patient must be asked to return for a repeat of the exam, it is a hardship for the patient and an expense to the health care provider. Other consequences include delays in report turnaround and increased liability exposure to the medical personnel and facilities.

A shortage of technologists means that there are many young and less experienced technologists being relied upon to make good decisions on a consistent basis even in a difficult work environment. In the past, radiologists have been able to instruct technologists and help them continually learn from their good and bad decisions; however, with the increased workloads that radiologists are experiencing and the tighter exam schedules that technologists are managing, there is less time for this kind of interaction. Communication between technologists and radiologists is further diminished by the increase in the number of exams being performed in outpatient facilities. Many radiologists have never met some of the technologists who submit exams to them for interpretation.

This dilemma and problem as described above is where experienced management must rise to meet and overcome the challenge. Radiologists are increasingly dependent upon management to communicate with the technologist when exam quality is compromised. Educators are doing all they can to produce qualified technologists; however, there is no substitute for experience and ongoing instruction. Technologists need constructive feedback on the quality of their work on a continual basis. Technologists also need accountability for the decisions they make. The sheer volume of exams and the dispersion of imaging locations make this a formidable task for management.

2. Prior Art

Historically, the prior art business methods to assess and improve quality for medical imaging have addressed few of these needs. Importantly, never has any prior art provided a solution in one system or method to virtually address all the above stated problems.

Examples of prior methods and apparatus to improve modern medical images begin with U.S. Pat. No. 5,655,084 issued to Pinsky, et al. (Aug. 5, 1997). This teaches an apparatus to convert medical images into a digital in order to transfer them to remote facilities. No mention of a system for improving the capability of the technologist or feedback from the radiologist to supervisor is addressed. A year later, another monitoring system patent was issued to Friz, et al. under U.S. Pat. No. 5,786,994 (Jul. 28, 1998). This patent taught a monitoring system to record errors and problems with a specific imaging machine or device. This data was then used to improve equipment maintenance in order to improve quality of the image. No technologist data or feedback was mentioned.

Other examples of data manipulation art for health facilities include a publication U.S. 2001/0032101 A1 provided by Statius Muller (Oct. 18, 2001). This teaches and describes a specific way to manage and store specific data on patients and an ability to retrieve the data rapidly. Again there lacks any discussion of using the data to improve the quality derived from individual technologists or departments. Another publication U.S. 2001/0051881 A1 provided by Filler (Dec. 13, 2001) teaches a system and method to transfer data from one location where a test or image was created to a remote location where a professional, such as a radiologist, might interpret the image. There is no mention of recording the image quality and potential causes of poor quality and relate that back to quality assessment and improvement for the technologist that created the image. A U.S. Pat. No. 6,353,802 issued to Barbur et al. (Mar. 5, 2002) teaches basic reject analysis through data gathering and statistical manipulation. This does reference radiology and photo processes but does not establish or provide any business method to incorporate the results into an improvement system involving the radiologist, technologist and supervisor. It is important for one to note that the radiologist's input is not required in this prior art. The new QAISys provides the methodology of taking any statistical data and creating a rating and manner to provide improvement to the human factors in the whole medical imaging business.

Another medical imaging system performance improvement tool is taught in publication U.S. 2002/0082864 A1 provided by Kelley et al (Jun. 27, 2002). This tool focuses on the equipment used and tracking of image quality. There is no discussion of the technologist's role in the medical imaging quality in respect to using any data to improve the technologist's capability. The publication U.S. 2002/0085026 A1 provided by Bocionek et al.(Jul. 4, 2002) is the pure data collection system in the radiology section of a health facility. This system now known as the Radiology Information System (RIS) primarily matches patient, doctor and imaging data into one system for convenient and rapid computer monitor access by medical personnel. The system permits text and image access and inputs but does not teach a technologist quality improvement system.

The publication U.S. 2002/0131625 A1 provided by Vining et al. (Sep. 19, 2002) teaches an intermediate comment or expert opinion from professional medical personnel such as radiologists and other medical doctors. This is supplemental to the Picture Archival and Communication System (PACS) and provides input to both the Radiology Information System (RIS) and Hospital Information System (HIS). While this may complement the new QAISys presented here, it does not teach or imply the use of the data inputted to improve the quality of the technologists' efforts. Another publication concerning a medical image improvement is a system taught by U.S. 2002/0194019 A1 by Evertsz (Dec. 19, 2002). This system teaches the use of known and unknown diagnosed problem case correlated and tested to determine if a radiologist could or has made a misdiagnosis. Technologist improvements are essentially not addressed.

The U.S. Pat. No. 6,574,304 B1 issued to Hsieh et al. (Jun. 3, 2003) teaches a computer aided system that takes existing medical images, analyzes the results by computer, re-determines if other concerns present themselves in addition to the original diagnosis, and even suggests the need for additional images. No technologist improvement data is suggested or taught. The U.S. Pat. No. 6,574,629 B1 issued to Cooke, Jr. et al. (Jun. 3, 2003) teaches the Picture Archiving and Communication System (PACS). This system is used to collect and present medical images but stops short of teaching its use of data collected to enhance technologists' capability.

The publication U.S. 2003/0212580 A1 provided by Shen (Nov. 13, 2003) teaches a system to manage the information flow within the medical imaging process. The publication discusses interfaces of the system and mentions analysis of organization performance, but does not elaborate on this in the description. Additionally, no claims for improvement to technologist's capabilities are provided. The publication U.S. 2004/0015372 A1 provided by Bergman et al. (Jan. 22, 2004) teaches a process to collect data in the medical information systems. It elaborates on patient and results information and statistical comparisons. It does not teach or claim using the data for improving capabilities and quality enhancement of the technologists in the medical image field.

None of the above described prior art teaches all the features and capabilities of the QUALITY ASSESSMENT and IMPROVEMENT SYSTEM (QAISys) in MEDICAL IMAGING.

SUMMARY OF THE INVENTION

This new business method is a QUALITY ASSESSMENT and IMPROVEMENT SYSTEM (QAISys) in MEDICAL IMAGING. The steps comprising this new method and the interface of the method to other health care information systems provide a complete manner to provide data and a way to enable greatly improved quality of medical images. The several features provided will be described below in the specification and with the accompanying drawings.

Key participants in the overall system:
  x. Medical Imaging Technologist or Technician—performs the work and inputs data relative to the patient and test conditions. (Note that different states have varying education requirements for imaging personnel. The terms Technologist and Technician are used interchangeably without regard to specific state requirements or education).

y. Radiologists—reads the image and inputs data relative to the quality of the image.

z. Medical System (Tech) manager or supervisor—reviews the data from the technologist and radiologist; strives to improve the performance of the technologist and the resultant images to the radiologist; and leads the overall process.

Key systems to query and interface with to get data and exchange information:

i. Existing PACS—Picture Archiving and Communication System(currently is normally linked to (ii).

ii. Existing RIS—Radiology Information Systems (currently is normally linked to (i) and (iii).

iii. Existing HIS—Hospital or Health Care Information System (currently is normally linked to (ii).

iv. QAISys—Quality Assessment and Improvement System (will be linked to (i), (ii) and (iii) for large, complex systems or is scalable to small operations with less volume of data processing.

OBJECTS AND ADVANTAGES

Accordingly, there are several objects and advantages of the QUALITY ASSESSMENT and IMPROVEMENT SYSTEM (QAISys) in MEDICAL IMAGING. One advantage of this method is that it facilitates efficient communication between technologists, radiologists and manager of technologists. The resultant databases provide specific information to pinpoint areas for individual and group improvement in the medical imaging field. It provides data by technologist, modality (type of image), location, equipment, and other demographic indicators. This data in turn is a basis for additional training and interaction among the staff. It permits a technologist to see progress in difficult areas as well as permitting radiologists and hospital staff to focus on specific needs of certain modalities that are below standard compared to other modalities for essentially all technologists. Managers may also have data for rewarding performance and evaluation of training needs.

Another advantage is the method provides and facilitates communication to other hospital and health care administration as to quality assessment and quality improvement for medical imaging departments. The system provides data to substantiate improvement as well as need for improvement to quality review groups, to certification activities, and to health care improvement public advocacy groups. The data demonstrates to all, including insurance carriers, Quality Improvement in the imaging field.

A further advantage is the beneficial impact to health care costs. Improved quality of the images result in fewer "retakes" of the test and removes the duplication costs that the health care provider often absorbs in its costs. Further, the liability exposure to radiologists, health care providers, and technologists should benefit from this improved quality. Patients themselves should ultimately receive better first time images and thus decrease their need for a repeat test. Though the patient may not bear the full cost of the actual test, the patient does bear the loss of time, cost of transportation and the time without the next logical medical procedure when tests are not performed properly the first time. Finally, health care providers, large hospitals or specific contract agencies, will have data to focus additional education and training for technologists. Thereby, un-needed education is avoided and the technologist is trained on the specific machines and procedures that that individual needs for improvement.

Another feature is that the improvement method focuses on the needs of the technologist. The results of the more complex tests; higher volume and testing frequency; the remote location of radiologists; and the fewer "seasoned" technologists to provide on-the-job training are less experienced personnel to educate and to train new technologists. This data rich new business method provides the focus and insight to improve the feedback to all technologists, to efficiently select the areas requiring improvement, and to permit the training to be focused on those requirements.

Another advantage is the system permits input by specific machine, by technologist, by modality, and by shift. If machine and equipment problems are more frequent for certain technologists or shifts, additional training or technical support may be considered to improve the test results for those conditions.

A further advantage is the QUALITY ASSESSMENT and IMPROVEMENT SYSTEM (QAISys) in MEDICAL IMAGING does not complicate or interfere with existing systems. The Picture Archiving and Communication System (PACS), the Hospital Information System (HIS), and the Radiology Information Systems (RIS) are not affected by the additional system. Outputs from those systems are used, but no inputs to those systems are compromised.

A still further advantage of improved quality of the service to the patient. Ultimately there are fewer re-takes of tests, fewer delayed diagnoses, and focus on specific modalities that need improvement as compared to others in a group of all the technologists.

An advantage to the implementation of this method as a fully integrated group of information systems is that the implementation benefits all the parties actually implementing and using QAISys in various important ways. Patients are assured that their chest x-ray, mammogram, brain MRI, or other medical imaging exam is performed to the satisfaction of the radiologist. Payers (insurance providers, employers, and patients) of the tests are benefited by reducing medical errors and by providing quick and accurate diagnosis which contributes to reduced healthcare costs. Referring Physicians that have access to images benefit from the improved image quality. Radiologists appreciate having their concerns with image quality addressed. Hospital Administrators are assured that they have provided a powerful tool to their radiology directors for maximizing quality and efficiency while reducing the liability exposure of the whole organization. Managers of technologists are enabled to readily identify and prioritize areas where improvements in image quality and workflow efficiency need to be made. Technologists are provided effective feedback as to their performance capability in order to improve their skill and provide better images to the entire health care system.

Finally, other advantages and additional features of the present QUALITY ASSESSMENT and IMPROVEMENT SYSTEM (QAISys) in MEDICAL IMAGING will be more apparent from the accompanying drawings and from the full description of the instant improvement method. For one skilled in the art of medical imaging and/or quality assessment and improvement systems, it is readily understood that the features shown in the examples with this instant method are readily adapted to other types of improvement methods for other health care systems and other industries.

DESCRIPTION OF THE DRAWINGS—FIGURES

The accompanying drawings, which are incorporated in and constitute a part of this specification, illustrate an embodiment of the present method that is preferred. The drawings together with the summary description given above and a detailed description given below serve to explain the principles of the QUALITY ASSESSMENT and IMPROVEMENT SYSTEM (QAISys) in MEDICAL IMAGING. It is understood, however, that the QUALITY ASSESSMENT and IMPROVEMENT SYSTEM (QAISys) in MEDICAL IMAGING is not limited to only the precise arrangements and instrumentalities shown.

FIG. 1 is a Diagram or flowchart of the existing PACS, HIS, and RIS system with the improved performance evaluation portion resulting in the QUALITY ASSESSMENT and IMPROVEMENT SYSTEM (QAISys) in MEDICAL IMAGING. FIG. 1A is the FIG. 1 with the various components and portions of the diagram indicated by their respective reference numbers (see below). This is QAISys interposed on a relatively large, complex health care facility with highly sophisticated information systems. FIG. 1B is the QAISys interposed on a relatively small, less complicated health care facility.

FIG. 6 is a picture showing a radiologist reviewing the results of a medical imaging test.

FIG. 7 is a table used by a radiologist to evaluate and feedback any dissatisfaction with the quality of the image.

FIG. 9A shows a technologist, a manager and actual images.

FIG. 9B shows a technologist and the manager reviewing data.

FIG. 9C shows a sketch of a review at a computer terminal.

FIGS. 10B and C are actual screens showing prototype results for radiologists and managers to review.

FIG. 12 is series of pictures and sketches of Quality Review meetings.

FIG. 12A is a group of colleagues reviewing data at a conference table.

FIG. 12B is sketch of a graphical presentation.

FIG. 12C is a group of medical personnel reviewing data.

FIG. 12D is a presentation to a certification team.

DESCRIPTION OF THE DRAWINGS—REFERENCE NUMERALS

Figure 1:
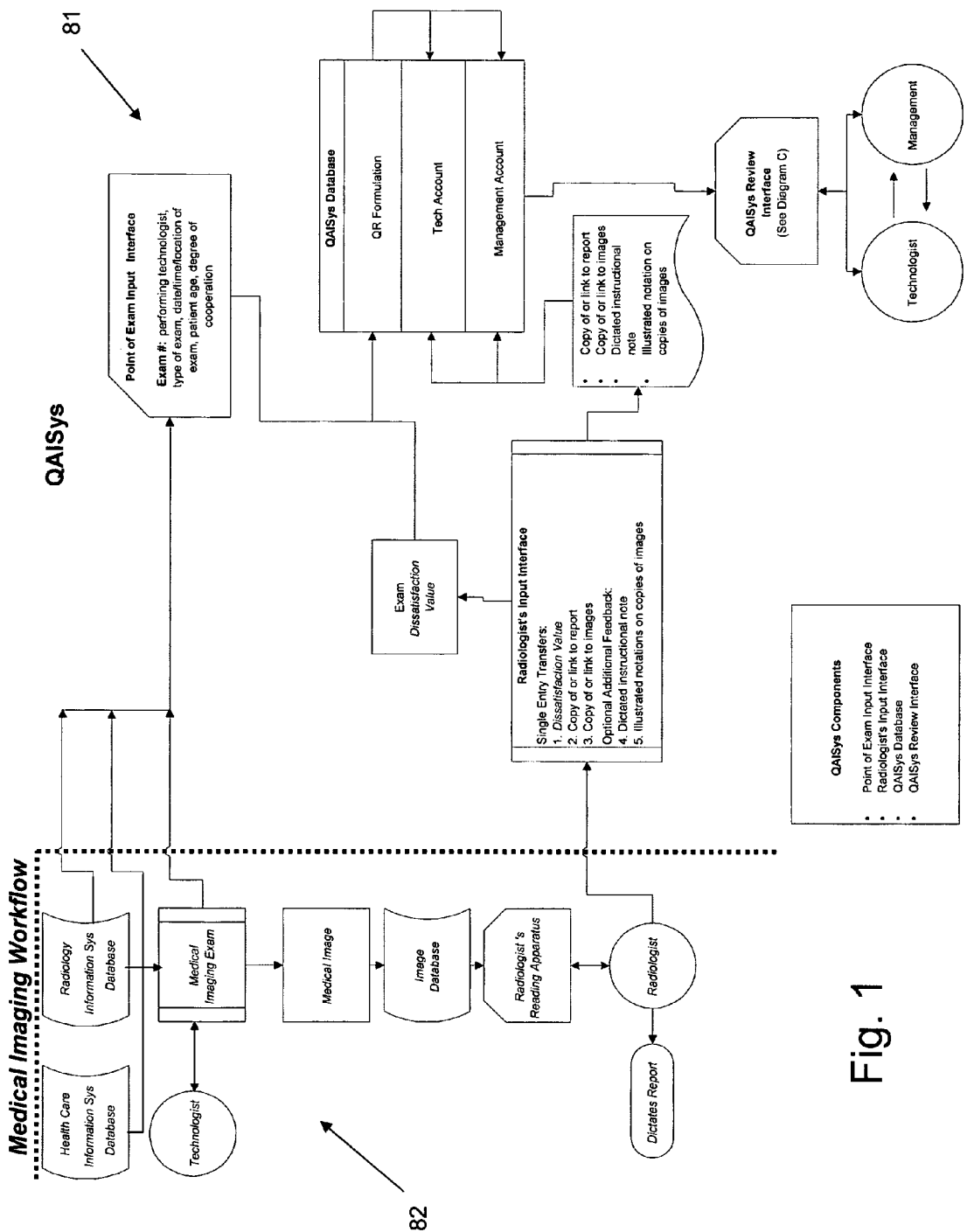

The following list refers to the accompanying pictures, tables, and drawings:

| | |
|---|---|
| 81 | New QAISys portion of method |
| 81A | Simplified QAISys for relatively smaller facilities |
| 82 | Existing Medical Imaging Workflow |
| 83 | Technologist |
| 84 | Radiologist |
| 85 | Manager or supervisor of Technologist |
| 86 | Image database [Picture Archiving and Communication System (PACS) or the like database] |
| 87 | Patient entry database [Health Care or Hospital Information System (HIS) or the like database] |
| 88 | Radiology Testing database [Radiology Information System (RIS) or the like database] |
| 89 | Point of Exam |
| 90 | Exam Dissatisfaction Value |
| 91 | QAISys resultant database |
| 92 | Means to formulate Quality Rating (QR) |
| 93 | Technologist Account within database |
| 94 | Management Account of all the data of all Technologists within the database |
| 94A | Management Account comparing QR by exam type (modality) |
| 94B | Management Account comparing QR of different Technologists in the Group for a specific exam type (modality) |
| 95 | QAISys review interface |
| 96 | Radiologist Dictation |
| 97 | Radiologist's input interface |
| 97A | Radiologist's input with supervisor assist |
| 98 | Patient ready for exam |
| 99 | Exam image (exemplary not limiting) |
| 100 | Management Account table of data comparing QR by exam type (modality) |
| 101 | Management Account graph depicting a comparison of QR by exam type (modality) |
| 102 | Management Account table of data comparing QR of different Technologists in the Group for specific exam type (modality) |
| 103 | Management Account line chart depicting a comparison of QR by Technologist for specific exam type (modality) |
| 104 | Health Care Quality Certification Review Team |
| 105 | QR modifier (generic or result of calculation) |

DETAILED DESCRIPTION OF PREFERRED EMBODIMENT

The present invention is a business method that permits Quality Assessment and Improvement specific to medical imaging in the health care industry. The method provides input and data information with respect to a technologist's performance, the condition of equipment, the type or modality of the test, and demographics about the patient. With this information, the technologist, his/her manager and the radiologist may interact to the data and provide direction, training and other appropriate actions to assure quality images for the patient and to improve the technologist's overall performance capability in providing those quality images.

The preferred embodiment of the method uses data and input from several interfacing systems. These existing systems include, but are not limited to, the inherent Hospital Information System (HIS) or its equivalent; the Radiology Information System (RIS) or its equivalent; and, the Picture Archiving and Communication System (PACS) or its equivalent. There are new data inputs possible from the technologist (point of exam) and from the radiologist (exam dissatisfaction value). Subsequently, QAISys may provide its own database from the data of the existing systems HIS, RIS and PACS and from the new inputs—point of exam and exam dissatisfaction value. This QAISys database is then manipulated to provide useful graphs, tables and other numerical analysis specific to a technologist's quality performance in providing medical images.

A person having ordinary skill in the field of quality assessment and improvement in the health care field appreciates the various systems, data inputs, data analysis, and resultant information that may be used to physically permit this business method to be accomplished. The improvement over the existing art is providing a method that interconnects a variety of systems and provides new important inputs from the radiologist and technologist to enable quality assessment and improvement to the medical images.

The improvements over the existing art are providing a business method that:
  A. facilitates efficient communication between technologists, radiologists and manager of technologists;
  B. facilitates communication of quality assessment and improvements to other hospital and health care administration;
  C. has a beneficial impact to health care costs;
  D. focuses on the needs of the technologist;
  E. provides a system that permits input by specific machine, by technologist, by modality, and by shift;
  F. does not complicate or interfere with existing systems; and
  G. provides improved quality of the service to the patient.
  H. benefits all the parties implementing and using QAISys in various important ways.

There is shown in FIGS. 1-12 a complete operative embodiment of the business method facilitated by QAISys—Quality Assessment and Improvement System. The embodiment generally relates a method to assure and improve the quality of medical images through improved capability by individual technologists performing the imaging exam. The same concept applies to other methods of quality assessment and improvement for the health care industry and industries where various people interact to provide services to a patient or client.

In the drawings and illustrations, note well that the FIGS. 1-12 demonstrate the configuration and use of a business method for improving the quality of medical images through improving the performance capability of the technologists that perform the image tests. Not all the types or modalities of the tests are discussed. This is for simplicity and should not detract from the full scope and spirit of this new business method.

Figure 1A:
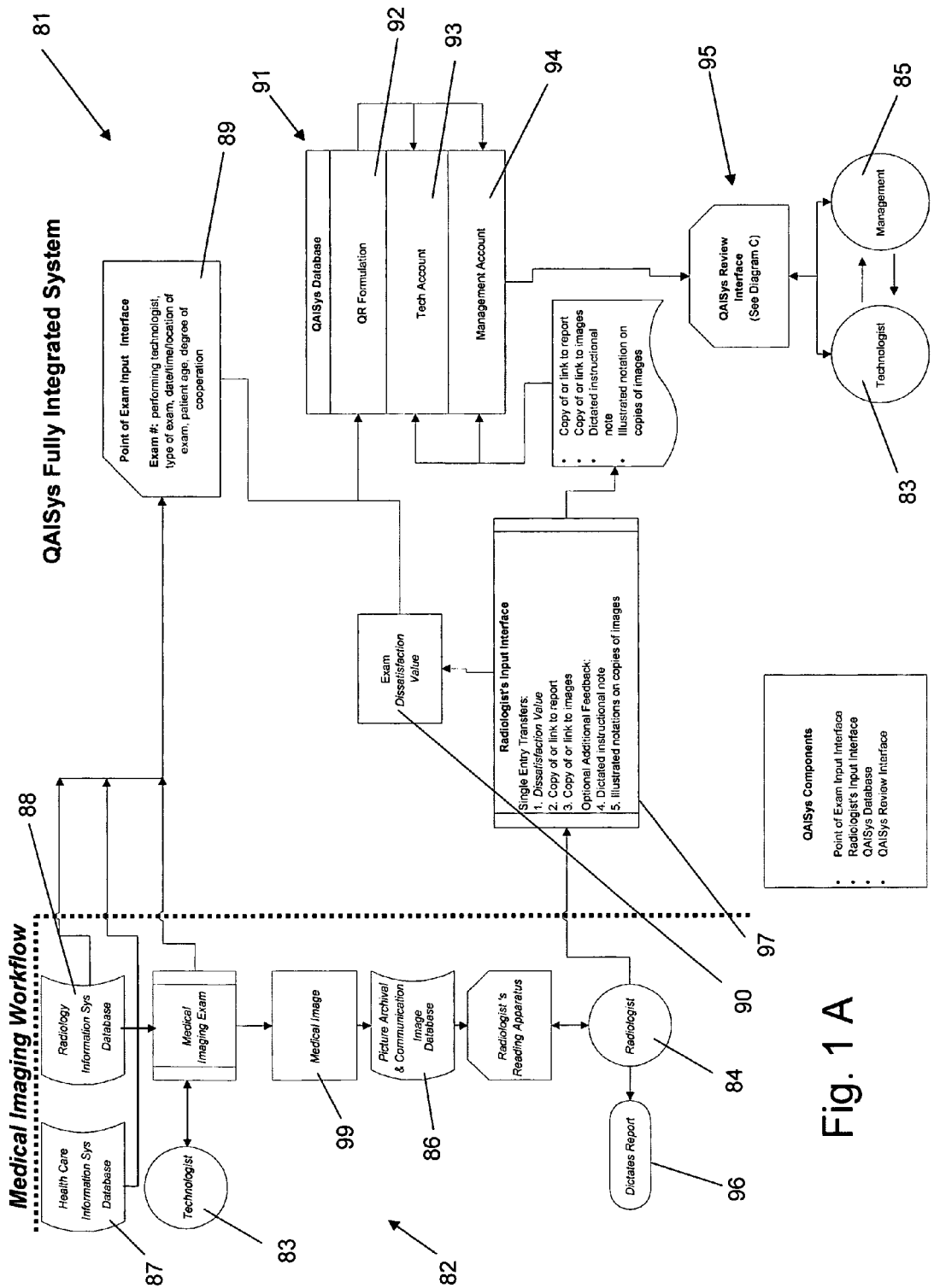

The preferred embodiment of the method is comprised of using data from the existing information systems of the health care facility and adding some additional data inputs specific to the quality of the image. FIG. 1 is a general diagram or flowchart of the existing systems workflow 82 with the improved performance evaluation portion 81 resulting in the QUALITY ASSESSMENT and IMPROVEMENT SYSTEM (QAISys) in MEDICAL IMAGING. FIG. 1A is the FIG. 1 with the various components and portions of the diagram indicated by their respective reference numbers. This flow method is QAISys interposed on a relatively large, complex health care facility with highly sophisticated information systems.

The preferred embodiment of the complex method incorporates part of the existing workflow 82. The existing workflow 82, normally includes a health care information system (HIS or the like) which has a database 87 of various patient information such as referring physician; patient demographics; health care history; administrative data such as admissions and billing information, etc.; and, other patient specific data. In the normal workflow 82 and specific to the medical imaging is included a system for tracking the radiology information (RIS or an equivalent) which also has a database 88. This radiology information database 88 contains text data of past examination history of a patient for other completed tests, such as number of images, series, radiation protection information, etc.; contains workflow drivers such as a work entry for a specific modality such as a CT, MRI, X-ray, etc.; and, contains other information for interfacing with a higher ranking information system (HIS) such as test completion date, number, and type of tests for billing and insurance requirements. The health care industry like other industries is transitioning most of its documentation to digital databases. This is true with the medical imaging portion of the industry. This has fostered the need and development of a archival and communication database 86 such as PACS or an equivalent. Here the digital record of the images are maintained. These digital files may then be easily transported, through computer-assist, to remote locations for review by the radiologist, referring physicians, other health care providers, or the like.

The preferred embodiment of the method also incorporates a new QAISys workflow 81. Here, there is a new QAISys database 91 that interfaces with the existing databases. The existing databases, described above, are such databases as the patient information and health care (HIS) database 87, the radiology information (RIS) database 88, and the image or digital picture archival and communication (PACS) database 86. These provide baseline data specific to an image, to the individual patient, to the health care facility, to the modality of the test, to the equipment used, to the radiologist 84 reading the image, to the technologist 83 performing the test, and the like. In addition to data from these systems, QAISys 81 receives data entry from a point of exam input 89 and from the radiologist 84 via a radiologist's input interface 97. This interface 97 provides a specific exam dissatisfaction value 90 as to a patient's image. These additional inputs are described below in detail.

The new QAISys database 91 utilizes the existing and new data in several ways. One utilization is an analytical means 92 to manipulate the data and to formulate a statistical quality rating for each exam. Another way is to maintain a specific account for an individual technologist 93. A further way is to provide a full account 94 for the manager of all the technologists. This manager account 94 provides data that may be analyzed and formulated and depicted in various manners such as by technologist groups, by modalities of the test, by the location of the facility, by the shift the test was performed, by the demographics of the patient set (age, gender, condition of health, etc.), and the like. One skilled in the art of statistical manipulation of data appreciates fully the plethora of analysis possible with this QAISys database 91. The QAISys workflow 81 also incorporates a QAISys review interface 95. At this interface 95, the technologist 83 and the manager 85 have an opportunity to review the quality rating QR of the technologist 83 and determine actions for improvement of the performance capability of the technologist 83. This is described in detail below in FIG. 3.

Figure 1B:
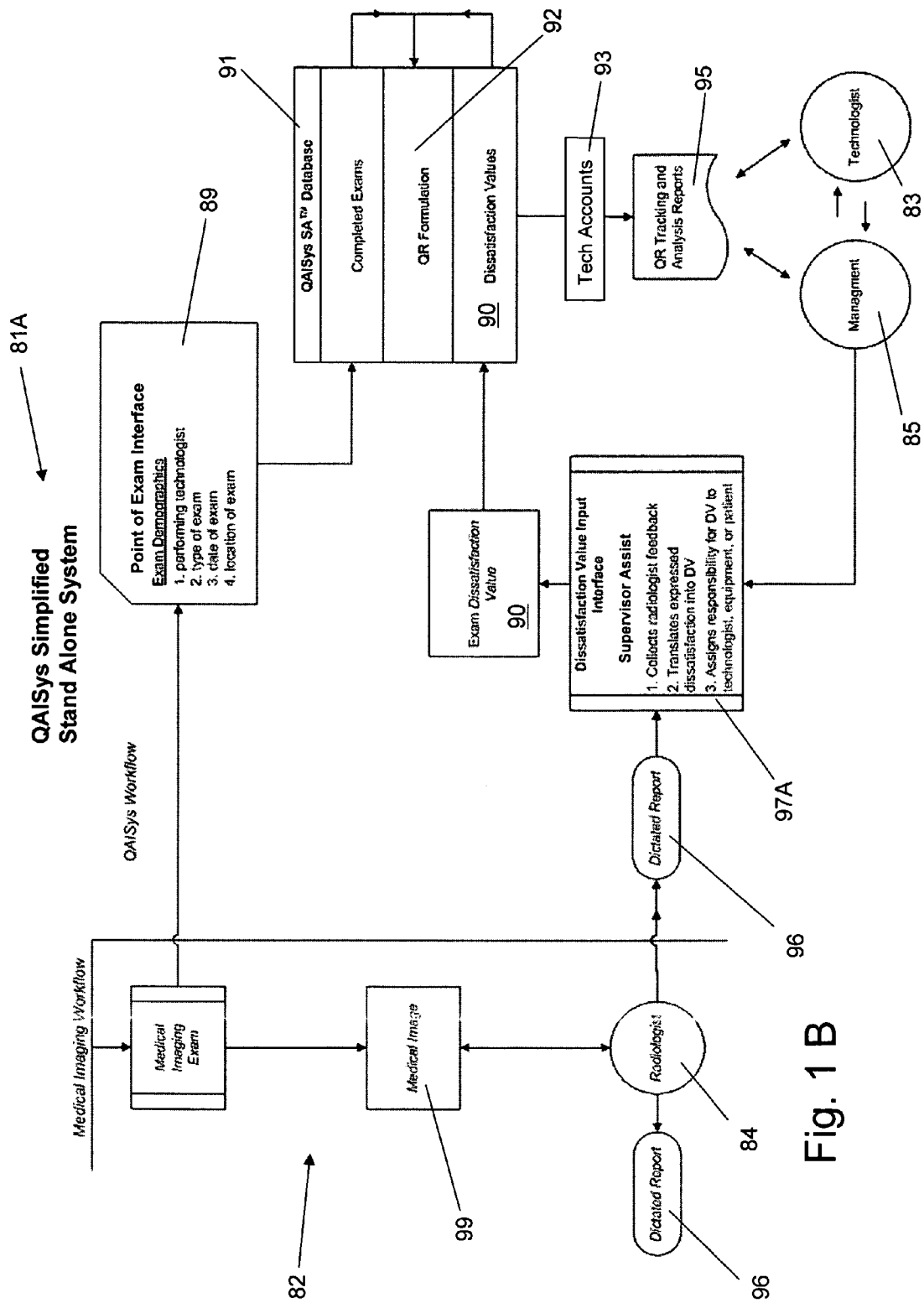

FIG. 1B is an alternative embodiment. Here the QAISys interposed on a relatively small, less complicated health care facility. The QAISys 81 is similarly interposed as a smaller, less complex QAISys standalone version 81A. Most of the work flow is the same. One skilled in the art and knowledgeable with medical facilities and medical imaging notes the major changes: an absence of the hospital information system 87 and/or radiology information system 88; a more simplified technologist 93 appended to the QAISys database 92; and a supervisor assist 97A to support the radiologist's 84 inputs. Tone skilled in the art of medical imaging and information systems well understands that the spirit and scope of this alternative, simpler version follows the full intent of the more complex version for larger health facilities.

Figure 2:
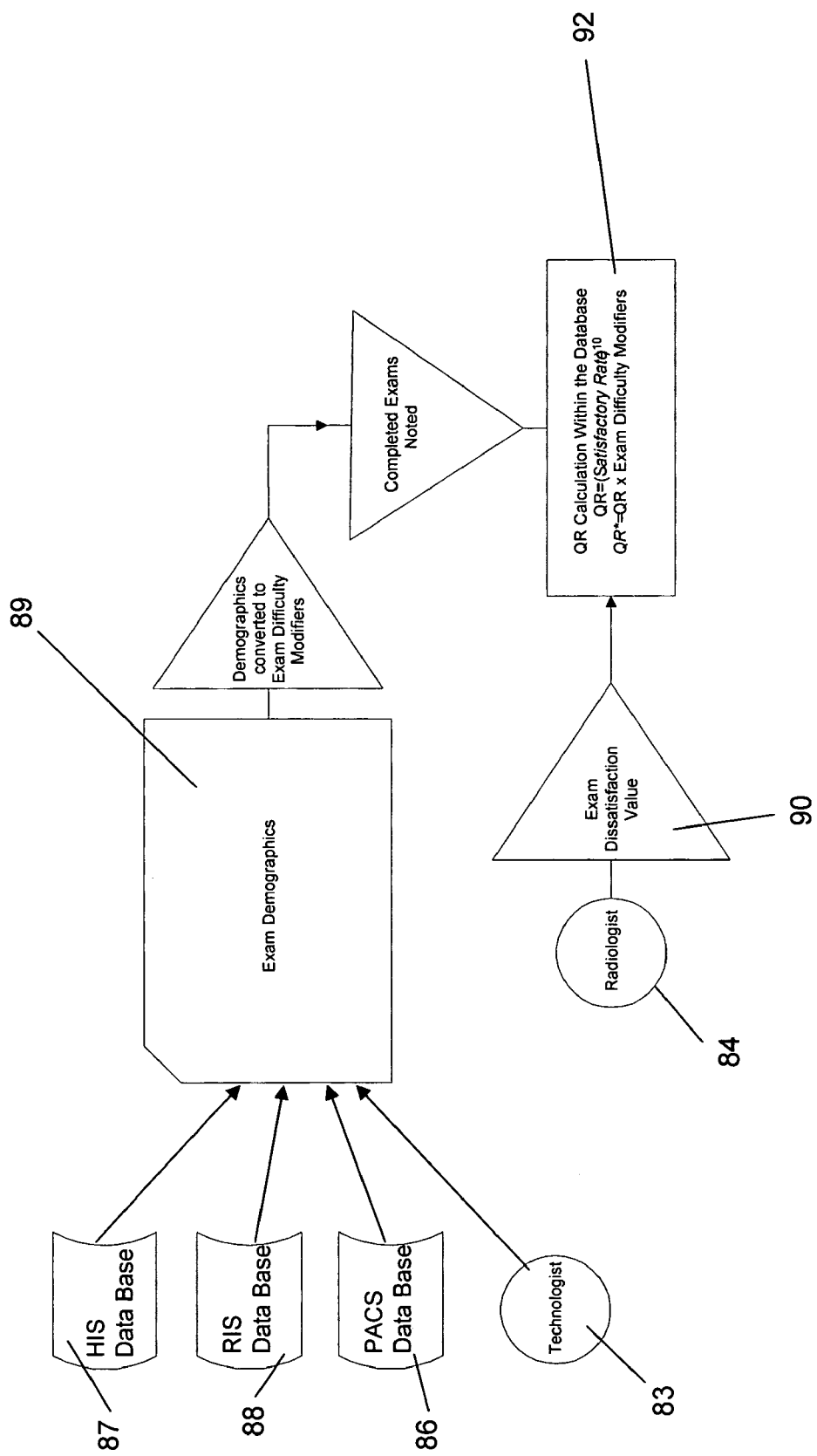
FIG. 2 is a flow chart showing the input from the technologist and the radiologist to the Quality Rating (QR) of the image.

FIG. 2 is another flow chart showing the data inputs to QAISys 81. Existing data systems, HIS, RIS, and PACS or the like may provide particular information with respect to the patient 98 that indicate specifics such as demographics, modalities of the tests, facility location, equipment, the radiologist 84 that reads the image, and the technologist 83 that performed the test. The data is extracted through a system interface from the HIS database 87, the RIS database 88 and/or the PACS database 86. One skilled in the art of extracting data from one computer system to another well appreciates the significant number of ways that the existing system data may be exported and preserved out of the existing workflow 82 and transferred to the QAISys workflow 81. Additionally, it is possible, but not preferred, to manually enter this patient and test specific data by an entry clerk, the technologist 83, or other health care personnel.

The above described data is available from the existing hospital databases or the manual entry. Therefore, at the point of exam input interface 89 demographics for every exam may be associated with an exam number (the patient's name is not necessarily required) and will include data such as date, time, location, type of exam, age of the patient, performing technologist, and exam difficulty factors expressed numerically (e.g. the degree of patient co-operation). This information is then sent to the performing technologist's account 93 and a manager's account 94 within the QAISys database 91.

The point of exam 89 data input is also then augmented by the radiologist 84 through the exam dissatisfaction value 90. Note well that the radiologist 84 in FIG. 1A inputs this value through the radiologist input interface 97. These data entries from existing systems 82, technologists 83 and radiologists 84 are all contained in the QAISys database 91. Then, the formulation means 92 to calculate or formulate a Quality Rating QR converts the data into a tangible rating for each test image specific to a patient 98 and technologist 83. This rating has any inputs from the radiologist 84 noted and tied/connected to the specific image.

An example of a formulation of a Quality rating (QR) is helpful. This is exemplary and not limiting since one skilled in the art or statistics and numerical analysis well appreciates the myriad of formulation means that exist. The example formulation is as follows:

From the Point of Exam Interface 89 and from the Radiologist Input Interface 97, the QAISys database 91 has the information it needs to compute a QAISys Quality Rating (QR). The QR is the unmodified expression of the degree of satisfaction that radiologists have with image quality. A QR can be tracked for the entire department or separately for each technologist, modality, location, or shift over any period of time. Analysis can be further refined to make comparisons by exam type or by time of day.

The components of the QR include:
1. The number of Completed Exams over a specified period of time (ce).
2. The Dissatisfaction Value 90 assigned to each unsatisfactory exam describing the degree of dissatisfaction.
3. The Dissatisfaction Factor (df), which is the sum of Dissatisfaction Values over a specified period of time.
4. The Unsatisfactory Rate (ur), which is the ratio of the Dissatisfaction Factor to Completed Exams expressed as a percentage.
5. The Satisfactory Rate (sr), which equals the inverse of the Unsatisfactory Rate.

The QR formula is expressed as follows:

$$QR = (sr)^{10}$$

where $(sr) = 1 - (ur)$
and $(ur) = (df)/(ce)$
then $QR = (1 - (df)/(ce))^{10}$

Figure 3:
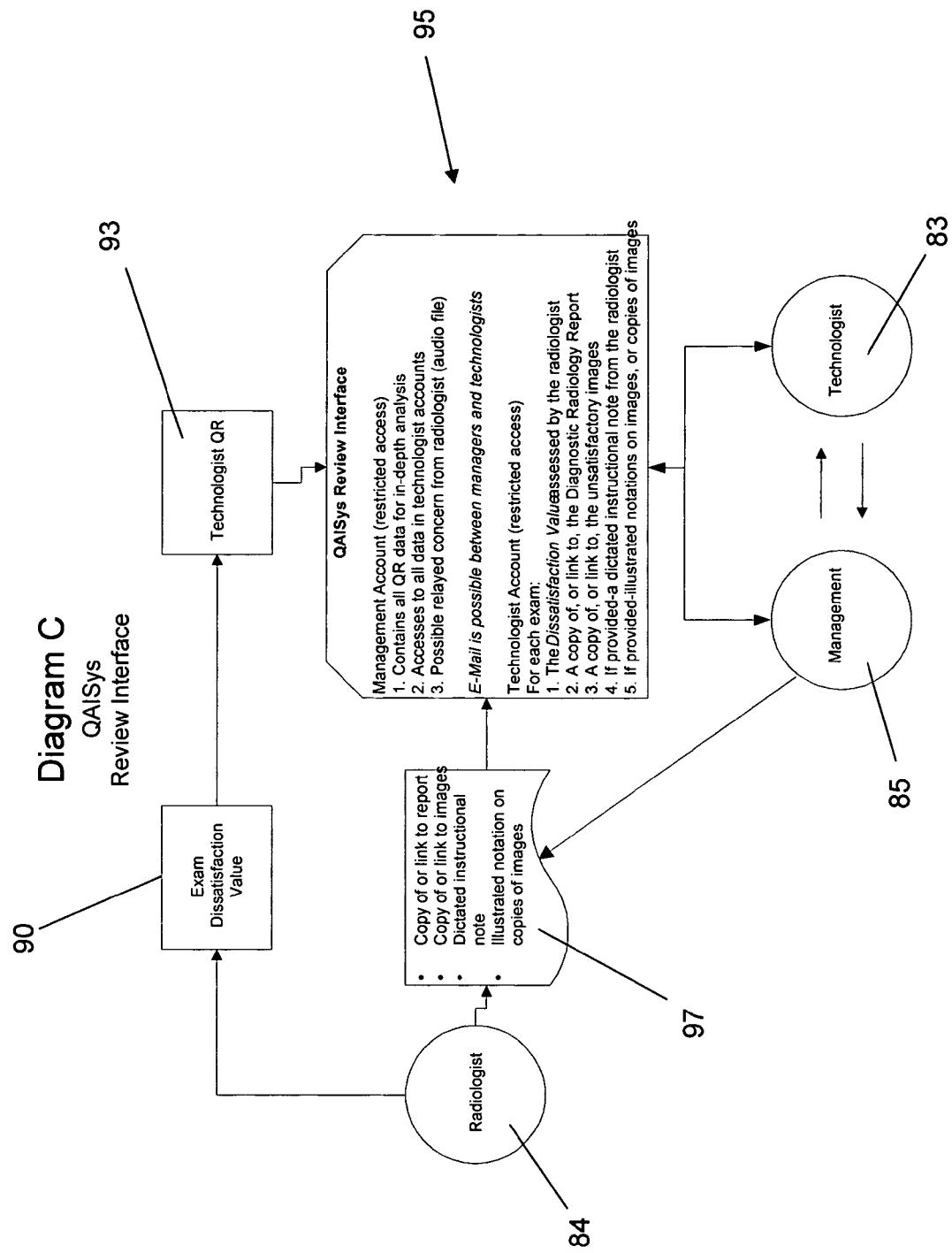
FIG. 3 is a flow chart of the radiologist input and the feedback portion of QUALITY ASSESSMENT and IMPROVEMENT SYSTEM (QAISys) between the technologist and his/her manager.

FIG. 3 is a flow chart of the radiologist 84 input and the feedback portion of QUALITY ASSESSMENT and IMPROVEMENT SYSTEM (QAISys) 81 between the technologist 83 and his/her manager 85. The radiologist 84 input is accomplished through the radiologist input interface 97. Here, the radiologist 84 may link a report to the image, dictate an instructional note, or place an illustration or note directly on the test image. Likewise, especially in small operations, the manager 85 may input data based on discussions with the radiologist 84 and the condition of the actual image. In addition, the radiologist 84 determines a dissatisfaction value 90, if appropriate, for the actual test image. The dissatisfaction value 90 is described in depth in FIG. 7, below. The dissatisfaction value 90 is a key input to the QAISys database 91 and is used by the Quality Rating formulation means 92 to establish a quality rating (QR) for each test image. The specific test image rating is then transferred and maintained in the QAISys database 92 in the respective technologist account 93.

The balance of the QAISys system 81 has a QAISys review interface 95. At the review interface 95, the technologist 83 and his/her manager 85 have the opportunity to interact with data from the test images. The interface 95 permits an in depth review of progress or deterioration of the Quality Ratings (QR) for the technologist 83 specific to the test that the technologist 83 has completed. This data provides a basis for the manager 85 and technologist 83 to assess the performance capability and determine an action plan to improve the rating. This action plan may include additional education, training, or special on-the-job training with experienced staff for test modalities that need improved. The action plans may indicate a special capability of the technologist 83 that needs to be shared and transferred to other technologists 83 in the group in order to improve the overall performance of the group.

Figure 4:
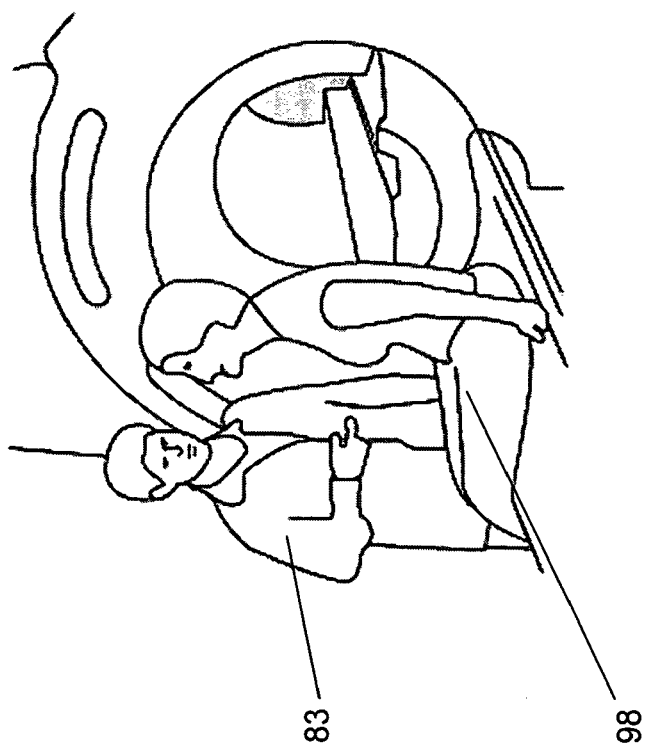
FIG. 4 is a picture of a patient and technologist ready for a test. Here the modality is an MRI.

FIG. 4 is a picture of a patient 98 and technologist 83 ready for a test. Here the test shown is an MRI. At or around this time is when the technologist 83 may determine the difficulty of a specific test modality, the cooperation and readiness of the patient 98, and other significant factors in order to input data into the point of exam interface 89 (not shown in this picture).

Figure 5:
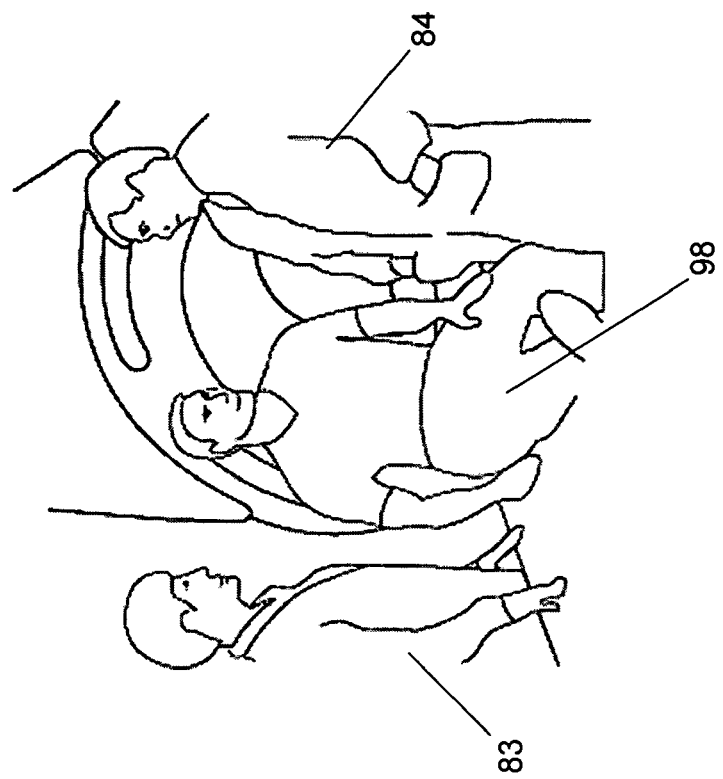
FIG. 5 is a picture of a patient, technologist, and radiologist discussing a test that is about to be run.

FIG. 5 is a picture of a patient 98, technologist 83, and radiologist 84 discussing a test that is about to be run. Often the radiologist 84 is remote from the actual test site and the technologist 83 completes the test and sends the image to the radiologist 84 via the PACS system or an equivalent system. This MRI test is exemplary and not limiting as to the modalities encompassed in the QAISys 81 method.

FIG. 6 is a picture showing a radiologist 84 reviewing the result of a medical imaging test 99. At this point, the radiologist 84 uses the radiologist input interface 97 to provide information respective to the image 99 and what the image 99 specifically denotes. This is an opportune time for the radiologist 84 to decide on the quality of the image and provide a dissatisfaction value 90, if appropriate, for the patient 98 and technologist 83 specific to the image 99.

FIG. 7 is an exemplary table that may be used by a radiologist 84 and manager 85 to timely evaluate and feedback any dissatisfaction value 90 with the quality of the image 99. The example (1, 2, or 3) is specific to the individual patient's exam and rates an image 99 as slightly compromised (1), moderately compromised (2), and severely compromised (3).

A simple numerically keyed entry—1, 2, or 3—determines a Dissatisfaction Value 90 per exam. The recommended values respective of the numeric entry are 0.5 for a slightly compromised image 99; 1.0 for a moderately compromised image 99; and 3.0 for a severely compromised image 99.

FIG. 8A is an example of a typical feedback schematic for a radiologist 84 to input evaluation data to the database for the image 99 that the radiologist 84 recently "read". This schematic represents an example of the detailed, drop-down menus that a radiologist 84 may use with the radiologist input interface 97. A person skilled in the art of computer programs and drop-down menus appreciates that this schematic drawing is exemplary of the plethora of ways to program the radiologist 84 feedback. FIG. 8B is one example of a screen that may be used in an actual prototype program. As an example, this schematic (FIG. 8A and screen FIG. 8B are meant to provide a way to present the scope and spirit of this part of the innovative method and not a limitation to the manner of implementing the actual systems. The radiologist 84 and supervisor 85 will work hand in hand to provide accurate and helpful data in evaluating a technologist's 83 deficiencies, training needs and progress. Other inputs to image quality may develop as technology progresses in the imagery field. For example, current development is underway to incorporate computer assisted diagnosing (CAD) in the medical imaging field. If utilized, the CAD system may provide the image quality dissatisfaction value 90 direct to the QAISys database 91 and still be within the spirit and scope of this new method.

Figure 9:
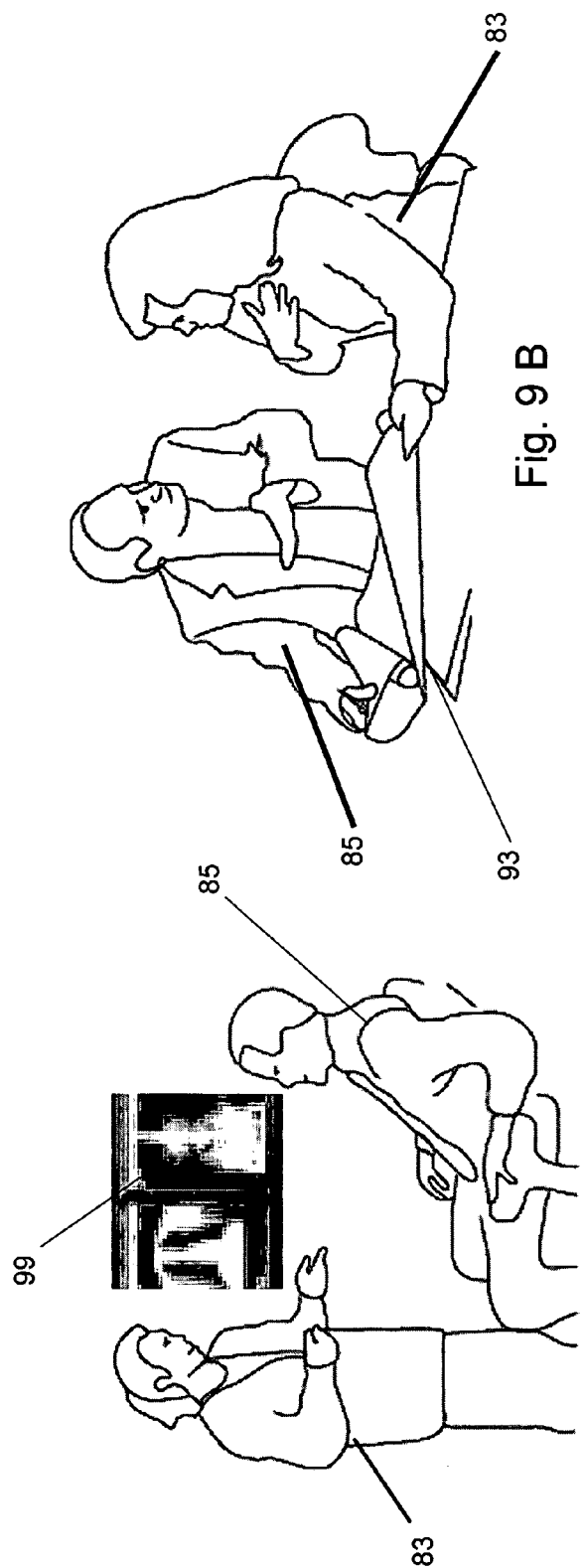
FIG. 9 is a series of pictures and sketches depicting a feedback step from manager to a technologist.

FIG. 9 is a series of pictures and sketches for feedback from manager 85 to a technologist 83. These are pictorial examples of the QAISys Review interface 97. FIG. 9A shows a technologist 83, a manager 85 and actual images 99. Likewise, FIG. 9B shows a technologist 83 and the manager 85 reviewing data from the individual technologist account 93. FIG. 9C shows a generic sketch of a review at a computer terminal between a technologist 83 and his/her manager 85. They are discussing data from the technologist's account 93.

Figure 10A:
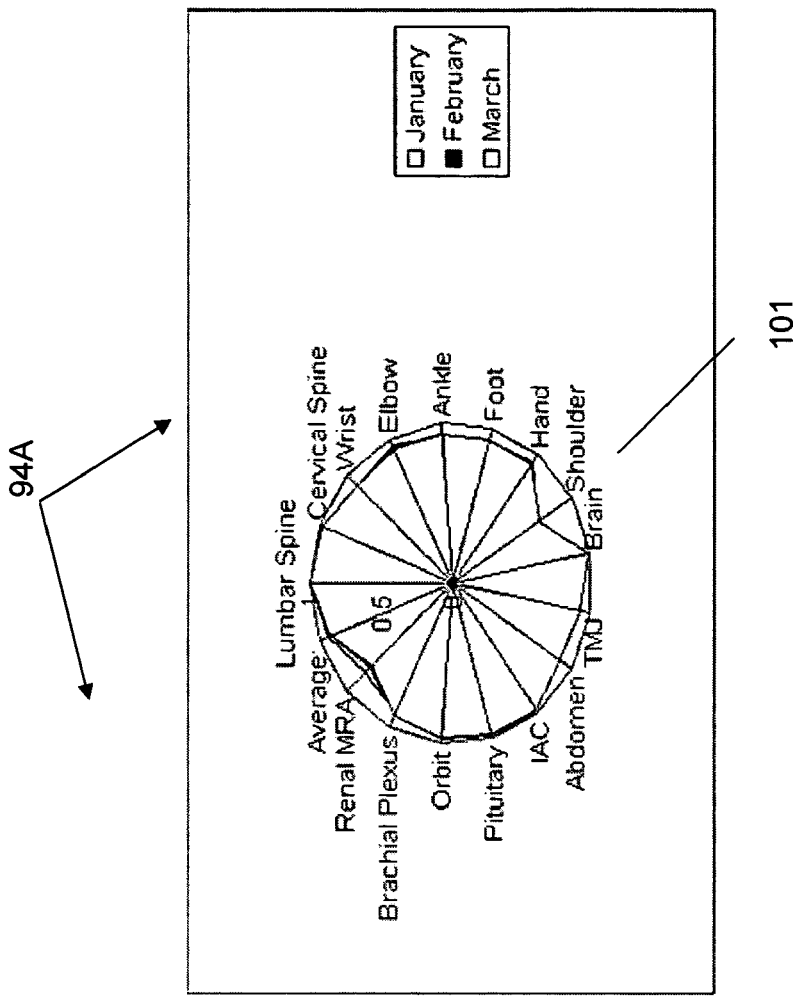
FIG. 10A is an example table and graph of data from a group of technologists by modality and Quality Rating (QR).
Figures 10B, 10C:
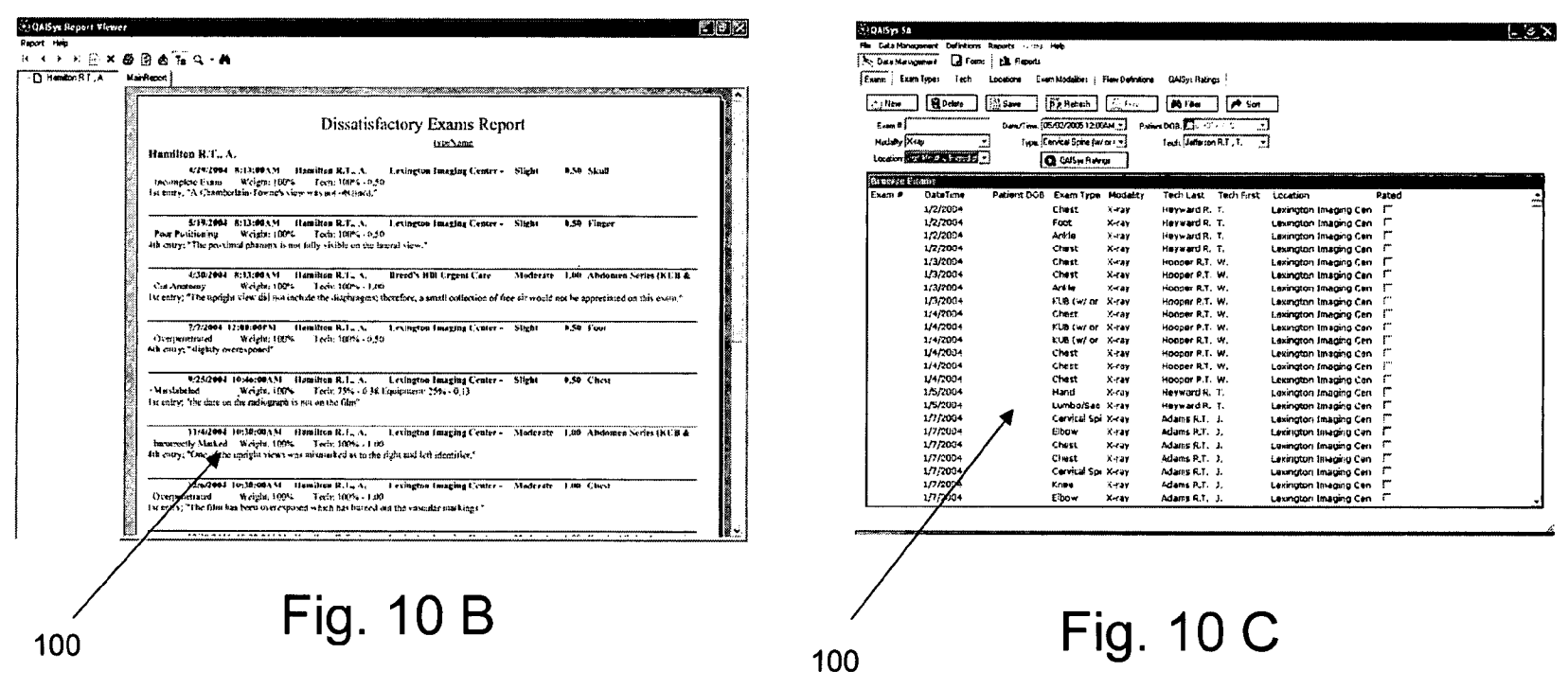

FIG. 10 is an example table 100 and graph 101 of data from a group of technologists by modality and Quality Rating (QR). Here, the compilation of data into the QAISys database 91 is captured and formulated by a statistical means 92. The results are transferred to the manager's account 94(A). That account, in turn, may be queried and statistically manipulated to provide data in order to generate comparison for tables, graphs and other numerical analysis presentations. FIGS. 10B and C are actual computer screens showing prototype results and input screens for radiologists 84 and managers 85 to review.

Figure 11:
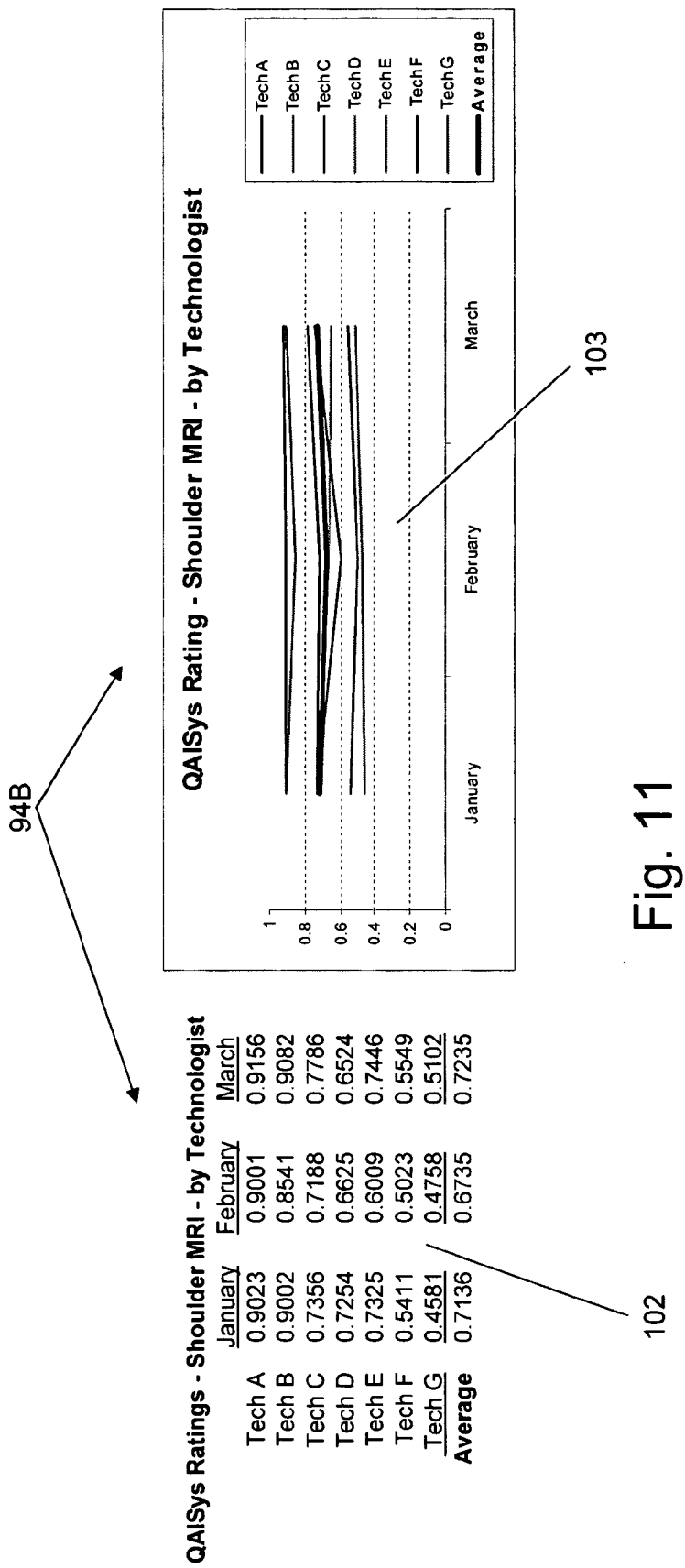
FIG. 11 is an example table and graph from a group of technologists for a specific modality and exam (here a shoulder MRI) and a Quality Rating (QR).

FIG. 11 is an example table 102 and graph 103 from a group of technologists for a specific modality (here a shoulder MRI) and a Quality Rating (QR). Like the previous example, this is a result of a specific query to the managers account 94(B).

FIG. 12 is series of pictures and sketches of Quality Review meetings. FIG. 12A is a group of colleague technologists 83 and their manager 85 reviewing data at a conference table. FIG. 12B is sketch of a graphical presentation of data from the manger's account 94 being made to either technologists 83 or health care personnel. FIG. 12C is a group of medical personnel (a technologist 83, a radiologist 84, and a manager 85 reviewing results of the data queries. FIG. 12D is a presentation by a manager 85 of technologists to a certification team 104. The availability of a data driven improvement system to address the assessment of quality images 99 and the continual improvement of those images may become key enablers to the certification and re-certification of health care providers.

This business method for medical image quality assessment and improvement—QAISys 81—provides that methodology and system.

The overall method and system described by the drawings and description is exemplified by the following:

| Step | Action | Exists | QAISys |
|---|---|---|---|
| 1 | Patient 98 goes to Doctor. | XXX | |
| 2 | Doctor prescribes tests (imaging required). | XXX | |
| 3 | Patient 98 registers at Hospital/Med clinic and data is entered into both RIS - Radiology information system 88 and HIS - Hospital Information System 87. | XXX | |
| 4 | Technologist 83 performs test, enters data in RIS 88 and enters digital image into PACS 86 (Picture Archive and Communication System). | XXX | |
| 5 | Technologist 83 at point of exam 89 enters demographics of patient, evaluation of patient/test compatibility, status of machine, and technologist's code into NEW QAISys (Quality Assessment and Improvement System) 81. | | XXX |
| 6 | Image 99 transferred to radiologist 84 - often at remote location. | XXX | |
| 7 | Radiologist 84 queries data from RIS 88 and PACS 86 for large facilities or small database for smaller facilities. | XXX | |
| 8 | Radiologist 84 evaluates image 99 for test and report. | XXX | |
| 9 | Radiologist 84 makes test results report (audio/transcribed), determines a dissatisfaction value 90, and enters various data into the interface 97 . . . | | XXX |
| 10 | Radiologist 84 evaluates quality of image from technologist 83 and enters into QAISys 81 the exam dissatisfaction value 90 - based on was it readable, does it need to be re-done, was it properly "centered", etc. This traditionally was done with some face-to-face review, now often the radiologist is remote and separated from the technologist. At this point the radiologist may supplement the rating with other dictated comments in respect to the quality of the image. | | XXX |
| 11 | QAISys data base 91 receives the normal data already in PACS 86 and RIS 88 and the two major new inputs:<br>1. From the actual test (from the technologist 83 at the point of exam 89) and<br>2. From the Radiologists 84 input as to the quality of the results - exam dissatisfaction value 90. | | XXX |
| 12 | With these inputs, a new QAISys data base 91 is created which has data on the capability and performance of the technologist 83 individually and as a group. | | XXX |
| 13 | QAISys database 91 is manipulated to give results in a manageable form. Normal statistics are performed by a means to formulate 92 a Quality Rating (QR). The results (numerical, graphical, and in descriptive messages) may be provided by category, by location, by modality, by individual technologist's code and the like. These results are a compilation of the specific the Quality Ratings (QR). | | XXX |
| 14 | Technologists 83 may query the data to see their individual results 93 and performance (and improvement or need for improvement). | | XXX |
| 15 | Managers 85 of the Technologist 83 query the same database 91. Managers 85 get individual and group data. The manager 85 has data to plan improvement training, provide reward opportunities, and provide information on critical shortfalls of certain technologists | | XXX |

-continued

| Step | Action | Exists | QAISys |
|------|--------|--------|--------|
|  | 83 (on specific test types, as a trend over a recent time, etc.) Thus, there is a continual Quality Rating (QR) for the group and the individual technologist. This specific rating enables management 85 to assure the quality of each technologist's 83 work or plan appropriate improvement measures. | | |
| 16 | Manager 85 has a face to face review 95 with the technologist 83 to address concerns and to plan quality/performance improvement. This is the QAISys Review Interface 95. This meeting has the Quality Rating (QR) based on the data. The data is from the radiologist 84 (exam dissatisfaction value 90)as to the image quality and from the technologist 83 (and/or other health care systems 86, 87, or 88) (point of exam 89) as to test conditions and results. | XXX | XXX |
| 17 | QAISys database 91 archives for a period of time and can also be truncated to reflect recent period and trends. | | XXX |

In the above preferred embodiment, the existing databases such as HIS 87, RIS 88, and PACS 87 or the like are currently found in many medium to large health care facilities. However, this method of using the existing system's data and augmenting it with the point of exam interface 89 data and the radiologist input interface 97 is not limited to facilities that only have these larger information and data storage systems. One skilled in the art of computer based business methods might see Appendix A for examples of these inputs by radiologists 84 at differently sized health facilities. it is important to think of QAISys as a flexible method. It can be implemented in a modular fashion so that it can be used in any medical imaging facility regardless of exam volumes and whether it is fully digitized or not. Each facility may use their own information systems and image archival systems to provide a method within the scope and spirit QAISys 81 and its methodology.

For example in the above preferred embodiment, there are no limitations to the size of the facilities. The method is fully scalable for different sized facilities. The indispensable component in QAISys is the database 91. In its simplest form, QAISys may consist of a database 91 installed on a PC and operated by management. This would be for very small facilities with low exam volumes. These facilities are more likely to be operating with conventional versus digital radiography. In this alternative embodiment form:

The data for the number of Completed Exams in the QR formulation can be extracted manually from RIS or exam logs and then manually fed to the QAISys database.

Radiologist input 97 can be extracted manually by reviewing radiology reports and then manually fed to the QAISys database 91.

QAISys database analysis can be performed, and reports generated by management and distributed in the form of a printed copy to technologists 83.

Unsatisfactory images can be obtained manually for review.

An alternative embodiment for intermediate sized facilities would be in a more advanced and versatile form. This alternative might consist of a QAISys database 91 that would serve as the foundation of a system that can be expanded with subsequent addition of automated inputs. It would be able to receive manual or automated data inputs from RIS database 88, allow multiple review QAISys interfaces 95 to be added, and could eventually be tied into a PACS database 86. This would be appropriate for small but growing imaging centers that do not yet have a PACS.

In another alternative embodiment, the QAISys 81 may be programmed directly in the RIS, HIS and/or PACS information systems. Here, the QAISys database 91 and points of entry may be entirely incorporated into the RIS, HIS, or PACS databases 88, 87, and 86. This may be somewhat complex for now, yet one skilled in the art of information systems and the programming of those systems appreciates the desire on some organizations to limit the number of information systems in the facility. Likewise, as the technology of information systems and digital images advances, the spirit and scope of this invention may be accomplished in a combined set of systems not yet available.

Still another alternative embodiment is to include tracking of the imaging equipment with respect to the quality of the images. QAISys 81 provides a means whereby equipment performance can be tracked and analyzed. Radiologists 84 can electronically tag exams affected by equipment malfunction at the time of reading. Technologists 83 can tag them at the time of the exam. Consistent equipment malfunctions will quickly become apparent. Affected exams will be readily available for review by clinical engineering personnel. Effectiveness of repair efforts can be monitored.

Another alternative embodiment is a modification or further refinement to the Quality Rating (QR). The usefulness of the QR for comparison purposes may be enhanced if clinical complications are factored into it via statistical modifiers 105. Values can be assigned to varying exam difficulty factors that affect image quality. The sum total of these values is then used to modify the QR creating a more comprehensive and equitable performance measurement. The ability to modify the QR may strengthen the analytical power of QAISys and can help to more accurately diagnose true underlying causes of image quality failures so that effective solutions can be implemented. Modifiers 105 can be tailored to each facility and/or modality. Examples of possible modifiers include:

Exam volume modifiers 105 (busy sites or shifts might need "volume" modifiers 105 to compare well with slower sites)

Patient co-operation modifiers 105 (sites that receive a high number of exams from pediatrics practices or nursing homes might need "patient co-operation" modifiers)

Exam complexity modifiers 105 (new exams, rarely performed exams, or otherwise complex exams may need "complexity" modifiers)

In the health care industry, there has been an increase in certification, especially focused on quality assessment and improvement. The scope and spirit of the method presented here may be transformed and modified to provide additional outputs and reports. These would provide and satisfy specific certification requirements or formatted data for the imaging organizations in a specific health care facility.

In total, all the points and details mentioned here throughout this detailed description of the drawings are exemplary and not limiting. Other components specific to describing a business method for quality assessment and improvement in the medical imaging may be added. A person having ordinary skill in the field of these types of business methods well appreciates this possibility of additions. The drawings and components have been focused on the parts shown in respect to the instant invention.

The new method for QUALITY ASSESSMENT and IMPROVEMENT SYSTEM (QAISys) in MEDICAL IMAGING has been described in the above embodiment. The manner of how the method operates is described below. Note well that the description above and the operation described here must be taken together to fully illustrate the concept of the new method for QAISys in MEDICAL IMAGING.

An example of building the QR begins with assigning Dissatisfaction Values 90 to each unsatisfactory exam based upon the radiologist's degree of dissatisfaction. For a sample variation, see FIG. 7, repeated here in the text as Table 2.

TABLE 2

Dissatisfaction Values

| Numeric Entry | Description of degree of dissatisfaction | Dissatisfaction Value per exam |
|---|---|---|
| 1 | slightly compromised (not noted on radiology report) | 0.5 |
| 2 | moderately compromised (noted on radiology report) | 1 |
| 3 | severely compromised (should be repeated) | 3 |

For example, a technologist 83 performs 200 exams in a given month. Two exams are considered "slightly compromised," one is considered "moderately compromised," and one is considered "severely compromised." The QR would be 0.7763.

1. Dissatisfaction Values 90 would be assigned in accordance with Table 2 as follows: 0.5 points for each of the "slightly compromised" exams; 1 point for the "moderately compromised" exam; and 3 points for the "severely compromised" exam.
2. The Dissatisfaction Factor (df) would be the sum of these values, or 5. (Table 3 illustrates this calculation process).

TABLE 3

Example creation of Dissatisfaction Factor

| Numeric Entry | Description of degree of dissatisfaction | Dissatisfaction Value per exam | Number of exams at each degree of dissatisfaction | Totaling the Dissatisfaction Factor |
|---|---|---|---|---|
| 1 | slightly compromised (not noted on radiology report) | 0.5 | 2 | 0.5 × 2 = 1 |
| 2 | moderately compromised (noted on radiology report) | 1 | 1 | 1 × 1 = 1 |
| 3 | severely compromised (should be repeated) | 3 | 1 | 3 × 1 = 3 |
| | | | Total Dissatisfaction Factor (df) = | 5 |

3. The Dissatisfaction Factor (df) is then divided by the number of Completed Exams (ce) and expressed as a percentage to equal the Unsatisfactory Rate (ur).

5/200=0.025 or 2.5%

4. The Satisfactory Rate (sr) is determined by subtracting the Unsatisfactory Rate (ur) from 100%.

100%−2.5%=97.5%

5. The Satisfactory Rate (sr) taken to the $10^{th}$ power equals the QR.

$97.5\%^{10}=0.7763$

6. The QR is 0.7763

Taking the Satisfactory Rate to the tenth power is important because it makes a clearer distinction between what might otherwise seem to be similar performances. Suppose another technologist 83, over the same month, also performed 200 exams but had a Dissatisfaction Factor of 10. This technologist's Satisfactory Rate would be 95%, which seems similar when compared to 97.5%; however, this technologist 83 had twice as much dissatisfaction indicated in their Satisfactory Rate. Factored exponentially, the QR for this technologist 83 would be 0.5987, which more appropriately indicates disparity in performance.

Figure 8:
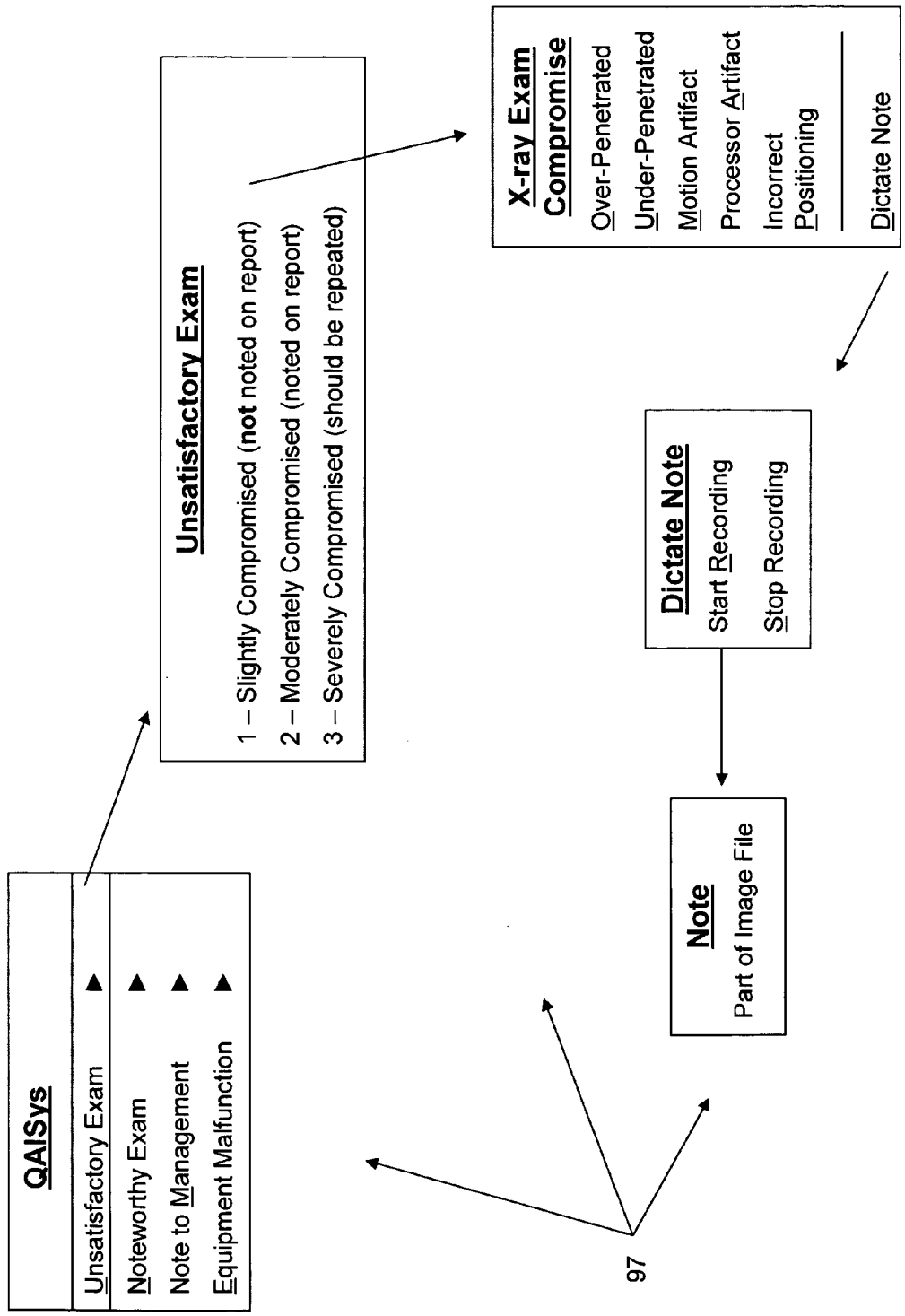
FIG. 8A is schematic and FIG. 8B is a prototype screen as examples of a typical feedback mechanisms for a radiologist to use to input evaluation data to the database for the image that the radiologist recently "read".
Figure 8:
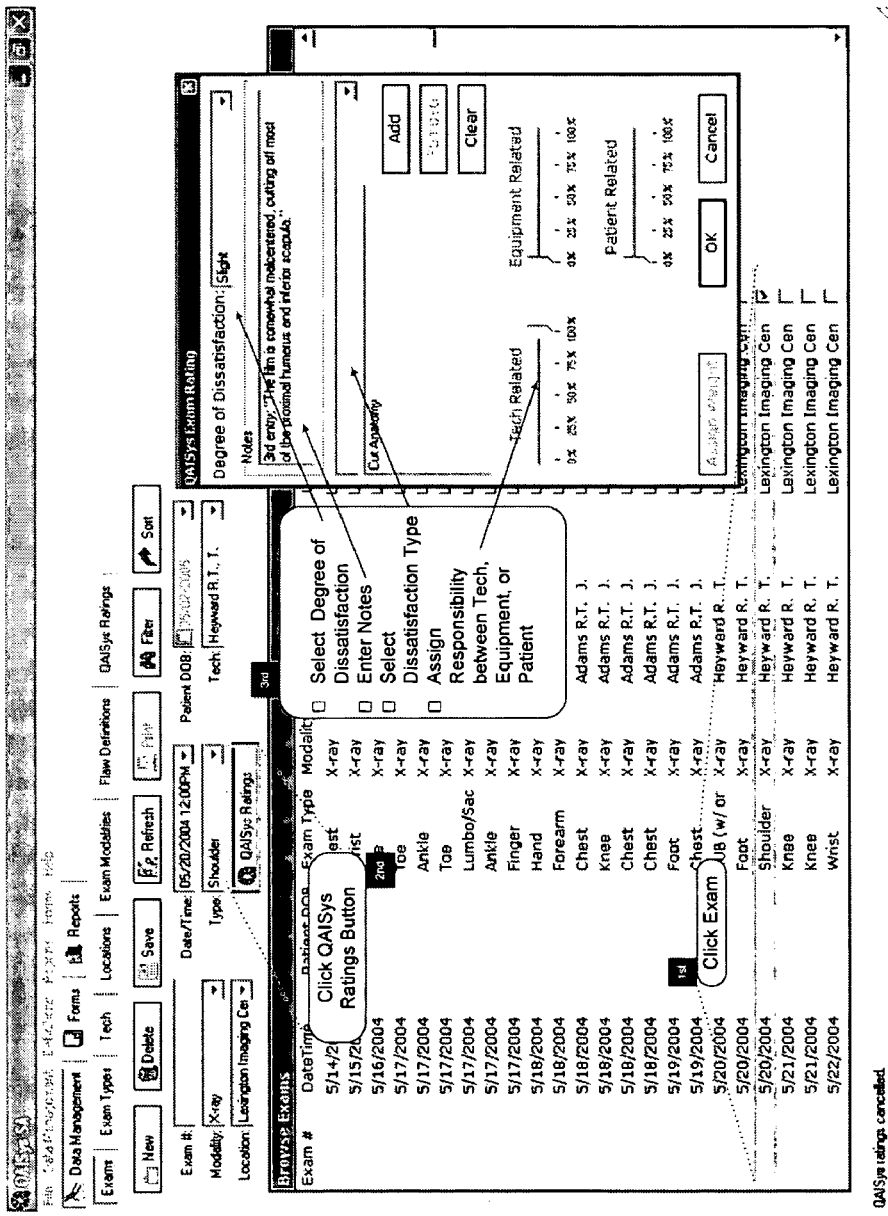

The FIGS. 7 and 8 demonstrate how a radiologist 84 may input data and benefit the improved methodology in this invention. The following is an example of how the Radiologist's Input Interface 97 can be designed to be user-friendly. It follows the sample of possible inputs presented in the text. (See Table 1 in FIG. 7 and repeated here).

TABLE 1

Radiologist has an opportunity to express his/her degree of dissatisfaction with an exam image at the time of reading the image and assign a Dissatisfaction value

| Numeric Entry | Description of degree of dissatisfaction | Dissatisfaction Value per Exam of dissatisfaction |
|---|---|---|
| 1 | Slightly Compromised (not noted on radiology report) | 0.5 |
| 2 | Moderately Compromised (noted on radiology report) | 1.0 |
| 3 | Severely Compromised (should be repeated) | 3.0 |

The software interface that the radiologist 84 uses while interpreting digital images incorporates a toolbar menu item entitled "QAISys", which opens a drop-down menu (see FIG. 8A).

These menu options then may open into subsequent menus. The "Unsatisfactory Exam" option opens a menu that offers the following options (see FIG. 8A).

For an Unsatisfactory Selection 1—"Slightly Compromised"—automatically sends the Dissatisfaction Value 90 assessed to the exam, and a copy of, or link to, the compromised images, to the technologist and management accounts 93 and 94; however, as indicated in the selection, the "slight" compromise in image quality is not mentioned on the dictated report. Therefore, it also may then open an option menu of "quick notes" or the like that will be sent with the exam in order to convey the nature of the radiologist's dissatisfaction in text. These notes are specific to the type of exam (x-ray, MRI, etc.). An example of the notes is shown as (see FIG. 8A).

These options will permit the radiologist 84 to quickly communicate the nature of the "slight" compromise by selecting the "Dictate Note" option. The radiologist 84 opens a box that provides options to "Start" and "Stop" recording an audio file that is also sent to the QAISys Database 91 accounts 93 and 94.

For an Unsatisfactory Selection 2—"Moderately Compromised"—and Selection 3—"Severely Compromised", the system automatically sends the following data to the technologist's and Quality Manager's accounts 93 and 94 within the QAISys Database 92:
1. The Dissatisfaction Value 90 as assessed to the exam;
2. A copy of, or a link to, the Diagnostic Radiology Report;
3. A copy of, or a link to, the compromised images.

Because the Diagnostic Radiology Report conveys the radiologist's dissatisfaction value 90 with the quality of the images, it is used to inform the technologist 83, thus, eliminating the need for further explanation. The other options within the "QAISys" drop-down menu use menus and dialogue boxes in a similar fashion. As stated in the present invention, if the development of Computer Assisted Diagnosing progresses to a high level of repeatability on reading the quality of images, that system may feasibly interface similar to the radiologist 84 for input to the QR database 91.

The FIG. 10 shows results of quality ratings QR as a graph 101 and tables of data 100 for a group of technologists 83 across all the modalities. FIG. 11 shows a table 102 and a graph 103 for a specific modality and compared the technologists 83. A systematic approach can be used in applying the information that QAISys 81 provides. With the Review Interface 95, management 85 has the ability to assess, compare, and track the performance of the entire department; or each site, shift, modality, or technologist 83. A manager 85 or a Quality Coordinator can generate reports and review analysis with radiologists 84, supervisors 85, and management teams. Goals can be set for improvement. Tactical approaches can be determined. Progress can be tracked. This all can also be done via e-mail for remote technologists 83 and managers 85.

An example or the analysis available from the graphs and tables in FIGS. 10 and 11 is helpful to understanding the operation of the new method. In-depth analysis of QRs can readily identify effectual, cost-effective means for improving image quality. The QRs can be reviewed with or without individual modifiers 105. This is extraordinarily helpful for evaluating areas such as appropriate shift lengths, need for additional staffing, need to improve process efficiencies, or a need for additional leadership or training at a site or for a modality. The compilation of statistics from the QR database 91 can also track image quality deficiencies that are caused by equipment malfunctions.

Because management 85 is able to evaluate what types of exams are consistently unsatisfactory and compare the ratings among technologists 83 performing those types of exams, successful methods used by individual technologists 83 can be identified and more broadly implemented. In FIG. 10, for example, suppose a report on the quality of all MRI exams indicates that the QR for shoulder MRI is consistently low and needs improvement. Therefore, the Manager 85 reviews each of the unsatisfactory shoulder MRI exams over a period of time and discovers that motion artifacts are the predominant detraction. He/she then generates a report that compares the QR for each technologist's 83 shoulder MRI exams.

In FIG. 11 this comparison chart reveals that two technologists 83 have a significantly higher QR for shoulder MRI than the others. By consulting these technologists 83, the manager 85 finds that one technologist 83 has a unique way of instructing patients in a breathing technique that minimizes breathing motion artifacts. The other technologist 83 has an excellent method of positioning a patient 98 to minimize the likelihood of muscle spasms. So that these successful methods can be more broadly employed, these technologists 83 are asked to provide an in-service on shoulder MRI. Furthermore, temporary changes in scheduling are made so that they work with each of the other technologists 83 beginning with the technologists 83 that have the lowest QR for shoulder exams.

The alternative embodiment of adding QR Modifiers 105 for exams may operate in several manners with various types of modifiers 105 such as described above in Paragraph [0078] or the like. An example, and not a limitation, to the way this alternative operates is shown for one of those modifiers 105. Here a Patient Modifier 105 would be used as follows:

If the patient has a compromised ability to co-operate, then the degree of patient co-operation could be expressed numerically and sent along with the exam demographics to the database 91 accounts of the technologist 93 and manager 94. The exam data entry interface 89 could allow the technologist 83 to easily indicate "lack of co-operation" factors. Each factor would have an assigned value. A possible set of entries for modifiers 105 and assigned values are represented in Table 4.

TABLE 4

Patient Co-operation Modifier

| Numeric Entry | Description of Degree of Lack of Patient Co-operation | Difficulty Values per Exam |
|---|---|---|
| 1 | listlessness | 0.25 |
| 2 | inability to follow instructions | 0.5 |
| 3 | uncontrolable movement | 2 |
| 4 | combativeness | 3 |

Referring to the example for QR formulation in Paragraph (0073), above: If the technologist 83 who performed 200 exams with a Dissatisfaction Factor of 10 and a QR of 0.5987 works near a nursing home, then he/she might have completed exams with the following characteristics:
1. Four on patients who were listless
2. Three on patients who had involuntary movement from Parkinson's
3. Two on patients who were unable to follow instructions
4. One on a patient who was combative due to Alzheimer's.

This technologist's 83 final QR should reflect the increased difficulty associated with these exams. Using the difficulty values in Table 5, a difficulty modifier 105 can be developed.

TABLE 5

Example of patient Co-operation Modifier

| Numeric Entry | Description of Degree of Lack of Patient Co-operation | Difficulty Values per Exam | Number of Exams Performed with Each Degree of Modifier | Totaling the patient Co-operation Modifier |
|---|---|---|---|---|
| 1 | listlessness | 0.25 | 4 | 0.25 × 4 = 1 |
| 2 | inability to follow instructions | 0.5 | 2 | 0.5 × 2 = 1 |
| 3 | uncontrolable movement | 2 | 3 | 2 × 3 = 6 |
| 4 | combativeness | 3 | 1 | 3 × 1 = 3 |
| | | | Total Patient Co-operation Modiffier = | 11 |

In this example, the total patient co-operation modifier 105 would be 11 (0.25×4=1 for the listless patients, 2×3=6 for the patients who had uncontrollable movement, 0.5×2=1 for the patients who had difficulty following instructions, and 3×1=3 for the combative patient). See Table 5.

This modifier would be incorporated into the QR by adding this value to the total of Completed Exams. The modified QR (QR*). would be calculated as follows:

1. The Modifier Points would be added to Completed Exams (ce) to equal the Modified Completed Exams (mce).

200+11=211 Modified Completed Exams (mce)

2. The Dissatisfaction Factor (df) is then divided by the number of Modified Completed Exams (mce) and expressed as a percentage to equal the Unsatisfactory Rate (ur).

10/211=0.0474 or 4.74%

3. The Satisfactory Rate (sr) is determined by subtracting the Unsatisfactory Rate (ur) from 100%.

100%−4.74%=95.26%

4. The Satisfactory Rate (sr) taken to the $10^{th}$ power equals the Modified QR*.

$96.26\%^{10}=0.6154*$

5. The Modified QR* is 0.6154*

The modified QR* of 0.6154* provides a more comprehensive and equitable performance comparison than the QR of 0.5987.

This example is an over-simplistic example of what could be accomplished with modifiers 105. It is offered only to demonstrate how difficulty modifiers 105 enable QAISys to be customized. Customization of this alternative embodiment of the method enables management 85 to more equitably apply QR standards and expectations of performance for all of their technologists 83. Customization would probably be a task for management 85 to undertake with the assistance of system manufacturers. Modifiers 105 can range from simple to very complex. Some modifiers 105 may be created after further extensive studies on a large scale and then programmed into existing QAISys databases 91. Certain modifiers 105 would be dynamic if based upon constantly changing parameters such as exam volumes. Eventually, manufacturers of imaging technologies might be helpful by offering suggestions or even formulated modifiers for some of the exams possible with their technologies. Management would still be able to review QRs with and without modifiers 105.

An Appendix B entitled QAISys Reports, by Richard B. Dale is included as an addendum. The innovative portion of the QAISys methodology are examples and not limitations of the resulting reports available and are incorporated by reference as part of this Business Method QAISys.

These uses for the new method for QUALITY ASSESSMENT and IMPROVEMENT SYSTEM (QAISys) in MEDICAL IMAGING are merely exemplary and not limiting to the myriad of uses for a business method that is such as the present innovation. The QAISys—Quality Assessment and Improvement System has been described above in connection with what is presently considered to be the most practical and preferred embodiment of the business method for the health care industry. With this description it is to be understood that QAISys—Quality Assessment and Improvement System is not to be limited to the disclosed embodiment. On the contrary, the new method is intended to cover various modifications and equivalent arrangements included within the spirit and scope of the description.

APPENDIX A—RADIOLOGIST'S INVOLVEMENT

Radiologist input as Dissatisfaction Factor (DF) or radiologist input converted to Dissatisfaction Factor is the key component of formulating a QR. There will be a variety of means for accomplishing this depending on two key variables:

1. The level of technology used
2. The degree of desired involvement from the radiologist It should be noted that there is a correlation between the workload of the radiologist 84 and that of the technologist's supervisor 85. It should be noted that greater radiologist 84 involvement is less likely to be desired than lower radiologist 84 involvement and that increased radiologist 84 involvement is likely to be presented to him or her as optional for specific instances. It should also be noted that separately dictated notes (not to be included in the radiology report) might be desirable as a means of creating distinction between the medical record and feedback for training purposes.

Table 1, on the following page, describes foreseen possible options for the radiologist's 84 assessment of image quality to be input to a QAISys application. From left to right, the columns range from simple standalone software application based implementation to progressively complex options involving integration with RIS 88, HIS 87, and PACS 86. From top to bottom, the rows progress from low radiologist involvement to increased radiologist involvement.

| | Radiologist Involvement With Varying Forms of Application | | |
|---|---|---|---|
| | Standalone Software Application | RIS and/or HIS-Integrated Application | RIS and/or HIS/PACS-Integrated Application |
| Radiologist dictates dissatisfaction to radiology report | Most Likely Means Quality management staff will need to categorize/score the degree of dissatisfaction in order to convert it to DF and will need to classify the nature of the detraction and assign weight of responsibility between patient, equipment, process, or technologist responsibility. | Most Likely Means Quality management staff will need to categorize/score the degree of dissatisfaction in order to convert it to DF and will need to classify the nature of the detraction and assign weight of responsibility between patient, equipment, process or technologist responsibility, | Most Likely Means Quality management staff will need to categorize/score the degree of dissatisfaction in order to convert it to DF and will need to classify the nature of the detraction and assign weight of responsibility between patient, equipment, process, or technologist responsibility. |

-continued

Radiologist Involvement With Varying Forms of Application

| | Standalone Software Application | RIS and/or HIS-Integrated Application | RIS and/or HIS/PACS-Integrated Application |
|---|---|---|---|
| Radiologist dictates dissatisfaction to radiology report and uses single entry to electronically flag exam report for review. | N/A; however, a radiologist might become disciplined to follow a report dictation template where dissatisfaction is consistently indicated in a specific area of the report allowing quick/easy identification of exam reports containing notice of radiologist dissatisfaction. | Most Likely Means This might allow reports that contain notes of dissatisfaction to be sent to a quality manager and/or technologist e-mail account. Quality management staff will still need to categorize/score the degree of dissatisfaction in order to convert it to DF and will need to classify the nature of the detraction and assign weight of reponsibility between patient equipment, process, or technologist responsibility. | Most Likely Means This might allow reports that contain notes of dissatisfaction to be sent to a quality manager and/or technologist e-mail account. Quality management staff will still need to categorize/score the degree of dissatisfaction in order to convert it to DF and will need to classify the nature of the detraction and assign weight of reponsibility between patient equipment, process, or technologist responsibility. |
| Radiologist dictates a note separate from the radiology report dictation. | Possible: this would be a function of a facility/organization-specific process. | Possible; this would be a function of a facility/organization-specific process. Notes of dissatisfaction might be sent to a quality manager and/or technologist e-mail account, eliminating the need for all exams to be reviewed in order to identify dissatisfactory exams. Quality management staff will still need to categorize/score the degree of dissatisfaction in order to convert it to DF and will need to classify the nature of the detraction and assign weight of responsibility between patient, equipment, process or technologist responsibility % | Possible; this would be a function of a facility/organization-specific process. Notes of dissatisfaction might be sent to a quality manager and/or technologist e-mail account, cdiminating the need for all exams to be reviewed in order to identify dissatisfactory exams. Quality management staff will still need to categorize/score the degree of dissatisfaction in order to convert it to DF and will need to dassity the nature of the detraction and assign weight of responsibility between patient, equipment, process, or technologist responsibility. |
| Radiologist uses an input interface to categorize or score the severity of dissatisfaction (i.e. slight, moderate, or severe). | N/A | Possible; this would allow the radiologist the option of assigning DF to an exam without having to use undesirable terms to describe his/her dissatisfaction in the radiology report. It would also clear up potential ambiguities in some instances | Possible; this would allow the radiologist the option of assigning DF to an exam without having to use undesirable terms to describe his/her dissatisfaction in the radiology report. It would also clear up potential ambiguities in some instances. |
| Radiologist uses an input interface to categorize severity, and/or classify nature of detraction, and/or assign weight between patient, equipment, process, or tech performance related limitations. | N/A | Possible; this would allow the radiologist the option of assigning DF to an exam without having to use undesirable terms to describe his/her dissatisfaction in the radiology report. It would also dear up potential ambiguities in some instances. | Possible; this would allow the radiologist the option of assigning DF to an exam without having to use undesirable terms to describe his/her dissatisfaction in the radiology report. It would also clear up potential ambiguities insome instances. |

APPENDIX B—QAISYS REPORTS

This is a compilation of reports that QAISys allows the user to generate. Some are designed for general surveillance, some are designed for specific analysis, and some are designed to facilitate targeted improvement projects. The user will be able to compile a list of their favorite reports and tailor them to their preferences. This is done through a combination of templates and wizards designed to make it easy for the user to generate and organize the reports. All of these reports and ratings are time-specific. The user will specify the timeframe for each report, or selected group of reports, as it is produced.

I. Accuracy Confirmation Reports
    Exam Log Comparison Report
    Completed Exams Report
    Data Entry Audit Report
II. Dissatisfactory Exams Reports
    Director's Dissatisfactory Exams Report
    Supervisor's Dissatisfactory Exams Report
    Technologist's Dissatisfactory Exams Report
III. QAISys Rating (QR) Tracking Reports
    Director's QR Tracking Report
    Supervisor's QR Tracking Report
    Technologist's QR Tracking Report
    Exam-type Specific QR Tracking Report
IV. Quality Assessment Reports
    Exam-type QR Comparison Reports
    Modality Exam-type QR Comparison Report
    Location/Shift Exam-type QR Comparison Report
    Technologist Exam-type QR Comparison Report
    Exam-type Dissatisfaction Factor (DF) Comparison Reports
    Modality Exam-type DF Comparison Report
    Location/Shift Exam-type DF Comparison Report
    Technologist Exam-type DF Comparison Report
V. Quality Improvement Analysis Reports
    Detraction-specific Comparison Reports
    Modality Detraction-specific DF Comparison Report
    Location/Shift Detraction-specific DF Comparison Report
    Technologist Detraction-specific DF Comparison Report
    Exam-type-specific Detraction-specific Comparison Reports
    Modality Exam-type-specific Detraction-specific DF Comparison Report
    Location/Shift Exam-type-specific Detraction-specific DF Comparison Report
    Technologist Exam-type-specific Detraction-specific DF Comparison Report VI. Equipment Performance Assessment/Analysis Reports
   Equipment-related Dissatisfactory Exams Report
   Equipment QR Tracking Report
   Equipment-related Exam/Detraction-specific DF Comparison Reports
VII. Patient-related DF Reports
   Patient-related Dissatisfactory Exams Report
   Patient-related Detraction-specific Exam-specific DF Comparison Report
VIII. Time of Exam/Staffing Analysis Report
IX. Summary Reports
   Director's Summary Report
   Supervisor's Summary Report
   Technologist's Summary Report I. Accuracy Confirmation Reports Accuracy confirmation reports help the supervisor and the technologists verify the accuracy of the data input. Exam Log Comparison Report: a chronological listing of database entries for comparison with exam logs. This report is a simple listing of the demographics for each exam entered into the QAISys database. The demographics are sorted by location then by date and order of entry so that the report should match the exam log for each location. These reports should be made readily available to all technologists so that they are able to affirm the accuracy of data entry especially as it relates to assigning responsibility for each exam performed.

Report listing exam demographics on all exams entered into the database for each specific location for comparison with each location's log book Completed Exams Report: a chronological listing of the database entries grouped by location for all exams performed by a specific technologist.

This report is similar to an Exam Log Comparison Report. It should be presented to each technologist along with his/her Dissatisfactory Exams Report and QR Tracking Reports to enable them to verify their performance of the completed exams assigned to them.

Report listing exam demographics on all exams entered into the data for each technologist grouped by location and listed chronologically Data Entry Audit Report: a chronological record of all data entries and changes made including details such as date, time, and user.

II. Dissatisfactory Exams Reports

Dissatisfactory Exam Reports are used to communicate specifically which exams were dissatisfactory and why. They clarify the assignment of Dissatisfaction Factor between technologist, equipment, and patient-related issues for each exam.

Director's Dissatisfactory Exams Report: a chronological listing of all dissatisfactory exams performed within the entire department, grouped by modality, location, and/or shift. Each entry in this listing includes a breakdown on how each dissatisfactory exam was scored.

This report lists each of the dissatisfactory exams performed by a department grouped by location, modality, or shift. It shows how responsibility for Dissatisfaction Factor for each exam is dispersed between technologist performance, and equipment or patient-related factors. It also displays any notes attached to the entry by the supervisor.

Report listing all dissatisfactory exams grouped by modality, location, or shift including details on breakdown of scoring Supervisor's Dissatisfactory Exams Report: a chronological listing of all dissatisfactory exams within the same modality, grouped by location and/or shift. Each entry in this listing includes a breakdown on how each dissatisfactory exam was scored.

This report lists each of the dissatisfactory exams performed by a modality grouped by location or shift. It shows how responsibility for Dissatisfaction Factor for each exam is dispersed between technologist performance, and equipment or patient-related factors. It also displays any notes attached to the entry by the supervisor.

Report listing all dissatisfactory exams within the same modality grouped by location or shift including details on breakdown of scoring Technologist's Dissatisfactory Exams Report: a chronological listing of the dissatisfactory exams performed by a technologist with a breakdown on how each exam was scored. This report lists each of the dissatisfactory exams performed by a specific technologist over a specified period of time. It shows how responsibility for Dissatisfaction Factor for each exam is dispersed between technologist performance, and equipment or patient-related factors and it displays any notes attached to the entry by the supervisor. It is provided to the technologists regularly and may include a copy of the radiology report for each dissatisfactory exam. This communicates specific feedback from the radiologist to the technologist and indicates how the severity of the quality detraction influences the technologist's QR.

Report listing all dissatisfactory exams performed by the same technologist grouped by location or shift including details on breakdown of scoring III. QAISys Rating (QR) Tracking Reports A QAISys Rating is generated by comparing an accumulation of Dissatisfaction Factor with the number of related examinations completed over a specified period of time. It can be formulated for a specific type of exam, an individual technologist, a location, a modality, a shift, or an entire department. It can also be formulated to show recurrence of equipment failure or patient related difficulties as they negatively impact image quality. Formulating and tracking QRs is useful for defining performance standards, recognizing and encouraging excellent performance, focusing training efforts, identifying internal training resources, evaluating the effectiveness of processes, assessing equipment performance and needs, and evaluating staffing levels.

Director's QR Tracking Report: a report that tracks a QR for the entire department as well as individual QRs for each modality. The departmental QR and modality QRs are produced by comparing the Dissatisfaction Factor generated within the entire department, or by the modality, with the number of exams performed in the department or modality over a specified period of time. It is useful for setting departmental goals and tracking progress.

Includes a daily, weekly, or monthly listing of the departmental QR
   Includes a line graph comparing/tracking the department's QR on a daily, weekly, or monthly basis
      "Threshold" (to be entered by user) is indicated by a strait line
      "Average" (to be calculated) is optionally indicated by a strait line
      "Goal" (to be entered by user) is indicated by a strait line
   Includes a daily, weekly, or monthly listing of the QR for each modality Includes a line graph comparing/tracking each modality's QR on a daily, weekly, or monthly basis
    "Threshold" (to be entered by user) is indicated by a strait line
    "Average" (to be calculated) is optionally indicated by a strait line
    "Goal" (to be entered by user) is indicated by a strait line Supervisor's QR Tracking Report: a report that tracks a QR for the entire modality as well as individual QRs for each location, shift, and technologist. The modality QR and location/shift/technologist QRs are produced by comparing the Dissatisfaction Factor generated within the entire modality, or by the location and/or shift, with the number of exams performed in the entire modality or location and/or shift over a specified period of time. It is useful for identifying areas where improvements can/should be made and tracking progress.

Includes a daily, weekly, or monthly listing of QRs for the entire modality
Includes a line graph comparing/tracking each modality's QR on a daily, weekly, or monthly basis
    "Threshold" (to be entered by user) is indicated by a strait line
    "Average" (to be calculated) is optionally indicated by a strait line
    "Goal" (to be entered by user) is indicated by a strait line
Includes a daily, weekly, or monthly listing of QRs for each location/shift
Includes a line graph comparing/tracking each location/shift QR on a daily, weekly, or monthly basis
    "Threshold" (to be entered by user) is indicated by a strait line
    "Average" (to be calculated) is optionally indicated by a strait line
    "Goal" (to be entered by user) is indicated by a strait line
Includes a daily, weekly, or monthly listing of QRs for each technologist
Includes a line graph comparing/tracking each technologist's QR on a daily, weekly, or monthly basis
    "Threshold" (to be entered by user) is indicated by a strait line
    "Average" (to be calculated) is optionally indicated by a strait line
    "Goal" (to be entered by user) is indicated by a strait line Technologist QR Tracking Report: a report that tracks a QR for each technologist. A technologist's QR is produced by comparing the Dissatisfaction Factor assigned to his/her exams with the number of exams performed by the tech over a specified period of time. It is useful for establishing accountability, assessing performance, setting goals for improvement, and tracking progress.

Includes a daily, weekly, or monthly listing of QRs for the technologist
Includes a line graph comparing/tracking each technologist's QR on a daily, weekly, or monthly basis
    "Threshold" (to be entered by user) is indicated by a strait line
    "Average" (to be calculated) is optionally indicated by a strait line
    "Goal" (to be entered by user) is indicated by a strait line Exam-type-specific QR Tracking Report: a report that tracks a QR for a specific exam-type. Exam-type QRs can be tracked by modality, location and/or shift, and/or technologist. This kind of report is useful once a specific exam-type has been targeted for improvement (see "Quality Assessment Reports" section on page 7).

Includes a daily, weekly, or monthly listing of exam-type-specific QRs for the modality as a whole
    Can be grouped by location
    Can be sorted by technologist
    Can be sorted from highest to lowest QRs
Includes a line graph comparing/tracking exam-type-specific QRs for the modality and for each location/shift
    "Threshold" (to be entered by user) is indicated by a strait line
    "Average" (to be calculated) is optionally indicated by a strait line
    "Goal" (to be entered by user) is indicated by a strait line
Includes a line graph comparing/tracking exam-type-specific QRs for the modality and for each technologist
    "Threshold" (to be entered by user) is indicated by a strait line
    "Average" (to be calculated) is optionally indicated by a strait line
    "Goal" (to be entered by user) is indicated by a strait line IV. Quality Assessment Reports QAISys enables comparisons to be made that reveal where improvement is most needed. Each exam-type can be compared by its' QR and/or by the Dissatisfaction Factor (DF) that it generates. Both comparisons are useful for prioritizing quality improvement efforts.

A. Exam-Type QR Comparison Reports

By comparing QAISys Ratings for each exam-type we are able to identify areas where improvement is most needed.

Modality Exam-type QR Comparison Report: a report that compares QRs for each type of exam performed within modality. The exam-type QR is produced by comparing the Dissatisfaction Factor generated for a specific type of exam with the number of times that type of exam is performed over a specified period of time. This report is useful for identifying exam-types that have high rates of quality failure relative to the frequency of their performance. These exam-types can then be analyzed so that the nature of the most frequently recurring detractions are revealed, the source of those detractions identified (technologist performance or equipment/patient-related factors), and appropriate solutions devised (targeted training, equipment upgrade, process improvement, staffing-level assessed) (see "Quality Improvement Analysis Reports" section).

Includes a listing of exam-types within the same modality and their QRs over a specified period of time
    Can be sorted from highest QRs to lowest
    Can be sorted by exam-type
Includes a bar graph comparing the QRs for each exam-type within the modality
    "Threshold" (to be entered by user) is optionally indicated by a strait line
    "Average of All Exam-types" (to be calculated) is optionally indicated by a strait line
    "Average Over Time for Specific Exam-type" (to be calculated on exams performed during a user-defined time period) is indicated within the bar on the graph for that exam-type
    "Record High and Low QR for a Specific Exam-type" (to be calculated) is indicated within the bar on the graph for that exam-type
    "Goal" (to be entered by user) is optionally indicated by a strait line Optional radar graph comparing the QRs for each exam-type within the modality
- "Threshold" (to be entered by user) is optionally indicated by symmetrical near-circular line
- "Average of All Exam-types" (to be calculated) is optionally indicated by symmetrical near-circular line
- "Average Over Time for Specific Exam-type" (to be calculated on exams performed during a user-defined time period) is indicated by an asymmetrical near-circular line
- "Record High and Low QR for a Specific Exam-type" (to be calculated) is indicated by two asymmetrical near-circular lines
- "Goal" (to be entered by user) is optionally indicated by a by symmetrical near-circular line Location/Shift Exam-type QR Comparison Report: a report that compares QRs for each type of exam performed at a specific location and/or during a specific shift. The Exam-type QR is produced by comparing the Dissatisfaction Factor generated for a specific type of exam with the number of times that type of exam is performed over a specified period of time. This report is useful for identifying exam-types that have high rates of quality failure relative to the frequency of their performance at a specific location. By comparing the QRs for exam types performed at a specific location with the average QRs for the same exam performed elsewhere, this report might indicate location-specific contributors to quality failures. These could be related to equipment or location-specific processes. They could also be related to patient related issues specific to the location. For instance, a location where a high volume of exams are performed on pediatric or geriatric patients might have lower QRs for specific types of exams due to patients decreased ability to cooperate with the technologists. Specialized training and/or improved immobilization equipment might be warranted.
- Includes a listing of exam-types and their QRs for a specified location and/or shift over a specified period of time
  - Can be sorted from highest QRs to lowest
  - Can be sorted by exam-type
- Includes a bar graph comparing QRs for each exam-type performed at the location and/or during the shift over a specified period of time
  - "Threshold" (to be entered by user) is optionally indicated by a strait line
  - "Average of All Exam-types" (to be calculated on exams performed during a user-defined time period) is optionally indicated by a strait line
  - "Average Over Time for Specific Exam-type" (to be calculated on exams performed during a user-defined time period) is indicated within the bar on the graph for that exam-type
  - "Record High and Low QR for a Specific Exam-type" (to be calculated) is indicated within the bar on the graph for that exam-type
  - "Goal" (to be entered by user) is optionally indicated by a strait line
- Optional radar graph comparing the QRs for each exam-type performed at the location and/or during the shift over a specified period of time
  - "Threshold" (to be entered by user) is optionally indicated by symmetrical near-circular line
  - "Average of All Exam-types" (to be calculated) is optionally indicated by symmetrical near-circular line
  - "Average Over Time for Specific Exam-type" (to be calculated) is indicated by an asymmetrical near-circular line
  - "Record High and Low QR for a Specific Exam-type" (to be calculated) is indicated by two asymmetrical near-circular lines
  - "Goal" (to be entered by user) is optionally indicated by a by symmetrical near-circular line Technologist Exam-type QR Comparison Report: a report that compares QRs for each type of exam performed by a technologist. The Exam-type QR is produced by comparing the Dissatisfaction Factor generated for a specific type of exam with the number of times that type of exam is performed over a specified period of time. This report is useful for identifying exam-types that have high rates of quality failure relative to the frequency of their performance. This can be helpful for the technologist to identify areas where they should focus on improving. Supervisors can use these reports to identify technologists who are performing well on exam-types that others in the department struggle with. These technologists might be helpful in providing training on those exam-types. Conversely, these reports also help identify the technologists who are not performing the exam-type well. These technologists might be scheduled to work with the technologists who perform the exam well for a time for the specific purpose of learning the better approach.
- Includes a listing of exam-types performed by a specific technologist and their respective QRs over a specified period of time
  - Can be sorted from highest factors to lowest factors
  - Can be sorted by exam-type
- Includes a bar graph comparing QRs for each exam-type performed by the technologist over a specified period of time
  - "Threshold" (to be entered by user) is optionally indicated by a strait line
  - "Average of All Exam-types" (to be calculated) is optionally indicated by a strait line
  - "Average Over Time for Specific Exam-type" (to be calculated on exams performed during a user-defined time period) is indicated within the bar on the graph for that exam-type
  - "Record High and Low QR for a Specific Exam-type" (to be calculated) is indicated within the bar on the graph for that exam-type
  - "Goal" (to be entered by user) is optionally indicated by a strait line
- Optional radar graph comparing the QRs for each exam-type performed by the technologist over a specified period of time
  - "Threshold" (to be entered by user) is optionally indicated by symmetrical near-circular line
  - "Average of All Exam-types" (to be calculated) is optionally indicated by symmetrical near-circular line
  - "Average Over Time for Specific Exam-type" (to be calculated on exams performed during a user-defined time period) is indicated by an asymmetrical near-circular line
  - "Record High and Low QR for a Specific Exam-type" (to be calculated) is indicated by two asymmetrical near-circular lines
  - "Goal" (to be entered by user) is optionally indicated by a by symmetrical near-circular line B. Exam-Type Dissatisfaction Factor (DF) Reports Dissatisfaction Factor (DF) is a score assigned to an exam if it is in some way considered dissatisfactory to the radiologist. DF reports are useful for showing the exam-types that generate the most severe and/or frequently recurring quality failures. They are not necessarily an indication of the most poorly performed exam type, but rather an assessment of poor quality with consideration to the exam volume. For example: "chest x-ray" might not have a lower QR than other exam types, however, it might generate the greatest frequency of quality failure because it is the most frequently performed exam. This will help managers, supervisors, and technologists to prioritize and focus quality improvement efforts appropriately; however, raw Dissatisfaction Factor is not useful for assessing or tracking performance since it is influenced by fluctuating exam volumes.

Modality Exam-type Dissatisfaction Factor Report: a listing of exam types performed within a modality, with the sum of the DF generated in the performance of each exam type over a specified period of time. This report will help managers decide if a particular exam should be targeted for improvement based on the severity and frequency of recurrence of quality failures. DF analysis is distinct from QR analysis in that it is not a per-exam rate but rather an assessment of poor quality with consideration to the exam volume.
- Includes a listing of all modality-specific exam-types and the sum of DF generated by each over a specified period of time
- Can be sorted from highest factors to lowest factors
- Can be sorted by exam-type
- Includes a bar graph or radar graph comparing DF for each exam-type generated within the specific modality over a specified period of time Location/Shift Exam-type Dissatisfaction Factor Report: a listing of exam types with the sum of their DF as performed at a specific location and/or during a specific shift. This report will help supervisors decide if a particular exam should be targeted for improvement based on the severity and frequency of recurrence of quality failures. DF analysis is distinct from QR analysis in that it is not a per-exam rate but rather an assessment of poor quality with consideration to the exam volume.
- Includes a listing of all exam-types performed at the location and/or during the shift and the sum of DF generated by each over a specified period of time
- Can be sorted from highest factors to lowest factors
- Can be sorted by exam-type
- Includes a bar graph or radar graph comparing DF for each exam type generated at the location and/or during the shift over a specified period of time Technologist's Dissatisfaction Factor Report: a listing of exam types with the sum of their DF as performed by each specific technologist. This report will help supervisors and techs decide if a particular exam should be targeted for improvement by the individual based on the severity and frequency of recurrence of quality failures. DF analysis is distinct from QR analysis in that it is not a per-exam rate but rather an assessment of poor quality with consideration to the exam volume.
- Includes a listing of each exam-type performed by a specific technologist and the sum of DF generated for each exam-type over a specified period of time
- Can be sorted from highest factors to lowest factors
- Can be sorted by exam type
- Includes a bar graph or radar graph comparing DF for each exam-type generated by the technologist over a specified period of time V. Quality Improvement Analysis Reports
Once an exam-type is targeted for improvement, in depth analysis of the nature of the detractions for that exam-type can reveal effective means of improving quality.

A. Detraction-Specific Comparison Reports

The nature of the detraction from image quality that causes radiologist dissatisfaction is indicated in the QAISys database. This allows us to compare the total Dissatisfaction Factor (DF) caused by different types of detractions. DF associated with a specific type of detraction can be compared for each modality, location and/or shift, or for each technologist. This is useful for determining patterns that may in turn suggest a means for improvement. For example, suppose an unusually high DF due to underexposure and overexposure in x-ray is demonstrated for a specific location. This may indicate a need for updates in technique charts. Or if one technologist at that location has a high DF due to under/overexposure and another tech working at the location doesn't, the tech with higher DF related to over/underexposure should probably use the same source of techniques as the tech with the lower DF related to over/underexposure.

Modality Detraction-specific DF Comparison Report: compares total DF associated with each type of detraction for exams performed within a specific modality over a specified period of time.
- Includes a listing of each type of detraction with the Dissatisfaction Factor that was associated with it for exams performed over a specified period of time across the entire modality
- Can be sorted by the type of detraction
- Can be sorted from the highest DF to the lowest
- Includes a pie graph presenting the proportion of DF generated by each type of detraction as compared to the total number of detractions
- Includes a bar graph comparing the DF generated by each type of detraction Location/Shift Detraction-specific DF Comparison Report: compares total DF associated with each type of detraction for exams performed at a specific location and/or during a specific shift over a specified period of time.
- Includes a listing of each type of detraction with the Dissatisfaction Factor that was associated with it for exams performed over a specified period of time at a specific location and/or during a specific shift
- Can be sorted by the type of detraction
- Can be sorted from the highest DF to the lowest
- Includes a pie graph presenting the proportion of DF generated by each type of detraction as compared to the total number of detractions
- Includes a bar graph comparing the DF generated by each type of detraction Technologist Detraction-specific DF Comparison Report: compares total DF associated with each type of detraction for exams performed by a technologist over a specified period of time.
- Includes a listing of each type of detraction with the Dissatisfaction Factor that was associated with it for exams performed over a specified period of time by a technologist
- Can be sorted by the type of detraction
- Can be sorted from the highest DF to the lowest
- Includes a pie graph presenting the proportion of DF generated by each type of detraction as compared to the total number of detractions
- Includes a bar graph comparing the DF generated by each type of detraction B. Exam-Specific Detraction-Specific DF Comparison Reports The specificity of detraction-specific DF comparison is increased if comparisons are narrowed to a specific exam type and compared by location or technologist. In our previous example, suppose one technologist at the location has a better set of techniques for rib detail (as indicated by a low DF generated by over/underexposure for rib exams) and another technologist has a better set of techniques for lumbar spine. The best techniques are combined to create or improve the standard technique chart.

Modality Exam-specific Detraction-specific DF Comparison Report: compares total DF generated by each type of detraction for a specific exam-type performed at all locations and during all shifts within a modality over a specified period of time.
- Includes a listing of each type of detraction for the specific exam-type with the sum of the DF associated with it over a specified period of time in the exams performed across the entire modality
- Can be sorted by the type of detraction
- Can be sorted from the highest DF to the lowest
- Includes a pie graph representing the proportion of DF associated with each type of detraction for the specific exam-type
- Includes a bar graph comparing the DF generated by each type of detraction for the specific exam-type Location/Shift Exam-specific Detraction-specific DF Comparison Report: compares total DF generated by each type of detraction for a specific exam-type for all exams performed at a specific location and/or during a specific shift over a specified period of time.
- Includes a listing of each type of detraction for the specific exam-type with the sum of the DF associated with it over a specified period of time in the exams performed at a specific location or during a specific shift
- Can be sorted by the type of detraction
- Can be sorted from the highest DF to the lowest
- Includes a pie graph representing the proportion of DF associated with each type of detraction for the specific exam-type
- Includes a bar graph comparing the DF generated by each type of detraction for the specific exam-type Technologist Exam-specific Detraction-specific DF Comparison Report: compares total DF generated by each type of detraction for a specific exam-type for all exams performed by a technologist over a specified period of time.
- Includes a listing of each type of detraction for the specific exam-type with the sum of the DF associated with it over a specified period of time in the exams performed by a technologist
- Can be sorted by the type of detraction
- Can be sorted from the highest DF to the lowest
- Includes a pie graph representing the proportion of DF associated with each type of detraction for the specific exam-type
- Includes a bar graph comparing the DF generated by each type of detraction for the specific exam-type VI. Equipment Performance Assessment/Analysis Reports Because Dissatisfaction Factor (DF) is sometimes associated with equipment-related causes, it is possible to track a QR for a specific location and make QR/DF comparisons that are useful for indicating and analyzing equipment deficiencies that contribute to lower QRs or elevated DFs. These reports are very useful for determining need for equipment repair or upgrade.

Equipment-related Dissatisfactory Exams Report: a listing of all exams performed at a specific location over a specified period of time where DF is associated with equipment malfunction and/or limitations. This report will be particularly helpful to clinical engineers responsible for maintaining equipment by enabling them to observe specific examples of equipment malfunctions.
- Includes a listing of each exam where DF was associated with equipment malfunctions and/or limitations at a specific location over a specified period of time Equipment QR Tracking Report: a report that tracks a QR for each location that is generated by comparing the DF that is associated with equipment malfunctions or limitations accumulated over a specified period of time, with the total number of completed exams performed at the location during the same period of time.
- Includes a line graph indicating the QR for the equipment at a specific location
    - "Threshold" (to be entered by user) is indicated by a strait line
    - "Average" for the modality is indicated by a strait line Equipment-related Exam/Detraction-specific DF Comparison Reports: Users may create reports that analyze equipment malfunctions and limitations in detail. DF comparisons can be exam and/or detraction-specific.

VII. Patient-Related DF Reports

Because Dissatisfaction Factor (DF) is sometimes associated with patient-related causes, it is possible to track a QR for a specific location and make QR/DF comparisons that are useful for indicating and analyzing recurrence and severity of patient-related DF. This is helpful because some locations may serve a patient population that requires special considerations in training and equipment. For example: a location may be in close proximity to a pediatrics practice and so it may have a lot of patients that require special immobilization equipment for adequate imaging. The technologists at that location may need to receive specialized training as well.

Patient-related Dissatisfactory Exams Report: a listing of all exams performed at a specific location over a specified period of time where DF is associated with patient-related difficulties.
- Includes a listing of each exam where DF was associated with patient-related difficulties at a specific location over a specified period of time Patient-related Detraction-specific Exam-specific DF Comparison Report: listing/comparison of each exam-type that has DF associated with patient-related contributing factors for each location.
- Includes a listing of each type of exam with the sum of the patient-related DF that was associated with it over a specified period of time for a specific location or for each technologist. This listing is grouped by the type of detraction.
    - Can be sorted by exam-type
    - Can be sorted by the type of detraction
    - Can be sorted from the highest DF to the lowest
    - Can be grouped by the exam-type
    - Can be grouped by the type of the detraction
- Includes a pie graph representing the proportion of DF for each type of detraction
- Includes a pie graph representing the proportion of DF for each type of exam

VIII. Time of Exam/Staffing Analysis Report

The time of exam can be entered in the exam demographics input interface. This makes it possible to analyze quality by grouping exams according to the time of day when they are performed and formulating a QR. This may reveal understaffing relative to regular spikes in exam volume. For example: suppose there is a low QR for exams performed between 6:00 AM and 7:00 AM, the volume of completed exams is also higher at this time. This might indicate a need to have a technologist come in to work a couple of hours early (at or just prior to 6:00 AM) in order to alleviate this staffing shortage. Subsequent improvement in the QR for this time of day would be expected.

Exam QR Tracking Report by Time of Exam: tracks/compares QRs for all exams performed during a specific time of day for any given location, modality, or technologist during a given period of time
- Includes a listing of QRs and CEs for each time interval
  - Can be sorted chronologically
  - Can be sorted from highest QR to lowest
- Includes a bar graph that compares QRs for exams performed during each specified time interval
  - Can be divided into various time intervals (i.e. 15 or 30 minutes)
  - Can be compared over an entire shift or 24 hour day
  - Includes a line indicating the number of exams completed ("completed exams" or "CEs") during each interval

IX. Summary Reports

Director's Summary Report: A customized compilation of reports designed to provide a general overview of the performance of the department.

Supervisor's Summary Report: A customized compilation of reports designed to provide a general overview of the performance of a specific modality.

Technologist's Summary Report: A customized compilation of reports designed to provide a general overview of the performance of a technologist.

The invention claimed is:

1. A computer-implemented method for determining at least one cause for production of unsatisfactory medical images produced within a set of medical imaging exams, the method comprising:
    (a) identifying one or more parameters capable of affecting said production of said unsatisfactory images:
    (b) assigning dissatisfaction values to said unsatisfactory images wherein said assigning involves assigning dissatisfaction values reflecting levels of dissatisfaction;
    (c) providing a computer generated correlation of a plurality of said dissatisfaction values for said set of medical imaging exams having a number of exams therein, and said one or more parameters identified to generate a numerical measure of dissatisfaction associated with said one or more parameters within said set of medical imaging exams; and
    (d) assigning said cause for said unsatisfactory images to at least one parameter based on said measure of dissatisfaction for the purpose of improving image quality by taking a corrective action related to said cause;
    wherein said providing a computer generated correlation involves generating a measure of dissatisfaction for said set of medical imaging exams which reflects a ratio of (a) a measure of dissatisfaction derived from said dissatisfaction values and (b) said number of exams within said set of medical imaging exams.

2. The method of claim 1, wherein said identifying includes identifying a nature of dissatisfaction as at least one parameter and said assigning cause for said unsatisfactory images involves assigning cause according to said nature of dissatisfaction.

3. The method of claim 1, wherein said identifying one or more parameters involves identifying one or more parameters selected from the group consisting of department, technologist, image modality, instrument, location, shift, time of day, exam type, and time interval.

4. The method of claim 3, wherein said assigning said cause involves choosing a measure of dissatisfaction selected from the group consisting of a dissatisfaction value, a dissatisfaction factor, an unsatisfactory rate, a satisfactory rate and a quality rating.

5. The method of claim 4, wherein said choosing involves selecting said quality rating and determining said quality rating from a formula comprising:

$$\text{Quality Rating} = (1 - df/ce)^{10}$$

where df is a sum of said dissatisfaction values, and ce is a sum of completed exams within said set of exams.

6. The method of claim 3, wherein said providing involves generating a quality rating wherein said quality rating reflects said ratio factored exponentially.

7. The method of claim 1, wherein said computer implemented method is implemented with a computer that is not part of a computer network.

8. The method of claim 1, wherein said computer implemented method is implemented with a multi-computer network.

* * * * *